United States Patent [19]

Nelson

[11] 4,189,937
[45] Feb. 26, 1980

[54] BOUNCELESS HIGH PRESSURE DROP CASCADE IMPACTOR AND A METHOD FOR DETERMINING PARTICLE SIZE DISTRIBUTION OF AN AEROSOL

[76] Inventor: Philip A. Nelson, 18615 SE. Covington Sawyer Rd., Kent, Wash. 98031

[21] Appl. No.: 821,608

[22] Filed: Aug. 3, 1977

Related U.S. Application Data

[63] Continuation-in-part of Ser. No. 464,158, Apr. 25, 1974, abandoned.

[51] Int. Cl.² ........................................... G01N 15/02
[52] U.S. Cl. .......................................... 73/28; 55/270
[58] Field of Search ............... 73/28, 432 PS; 55/270, 55/446

[56] References Cited

U.S. PATENT DOCUMENTS

| | | | |
|---|---|---|---|
| 3,001,914 | 9/1961 | Andersen | 73/28 |
| 3,693,457 | 9/1972 | Pilat | 73/432 PS |
| 3,771,291 | 11/1973 | Klingler | 73/432 PS |
| 3,795,135 | 3/1974 | Andersen | 73/432 PS |
| 3,983,743 | 10/1976 | Olin et al. | 73/28 |

OTHER PUBLICATIONS

Holland et al., "Three Multi Stage Stack Samplers", Chemical Engineering Progress, vol. 69, No. 6, pp. 93-95, Jun. 1973.

*Primary Examiner*—Stephen A. Kreitman
*Attorney, Agent, or Firm*—Thomas W. Secrest

[57] ABSTRACT

This invention is directed to a high pressure drop cascade impactor wherein the particles do not bounce from the collection plate; to a method for designing said impactor; a method for calculating and determining the particle size distribution of an aerosol wherein the particle size may have a Stokes (aerodynamic) diameter as small as 10 nanometers; and to a method of manufacturing such an impactor.

The impactor that is the subject of this invention is different from and superior to previously described impactors in the following principal respects:

1. The particles exhibit substantially no reentrainment, or bounce, from the collection surfaces. This property is achieved by (a) limiting the exit jet stream velocities such that the herein defined "bounce parameter", $\beta$, is never exceeded, and (b) increasing the thickness of the jet plates to elongate the jet passageways in order to reduce the jet velocities so that bounce will not occur.
2. The impactor described herein eliminates turbulence near the entrances to the jet holes by rounding the edges of the jet holes. This is accomplished on the small holes by means of electropolishing.
3. The impactor described herein is capable of capturing particles as small as 40 nanometers Stokes (aerodynamic) diameter. By contract, previously described impactors could capture particles only as small as 300 nanometers Stokes diameter.

23 Claims, 30 Drawing Figures

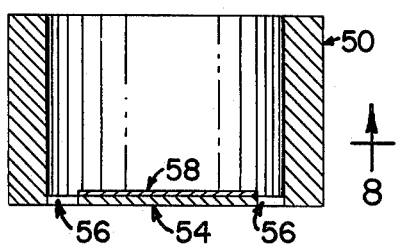
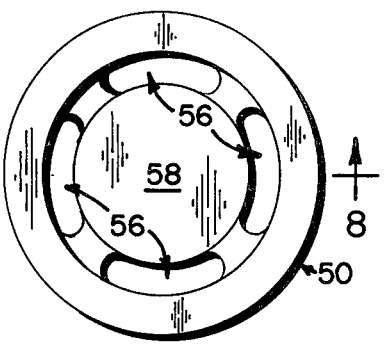
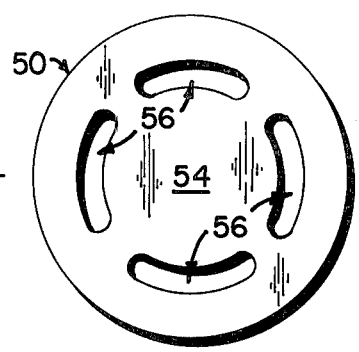
FIG. 8   FIG. 7   FIG. 9
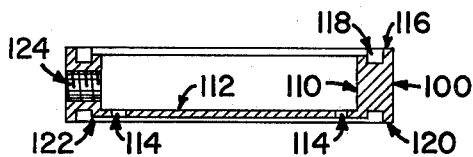
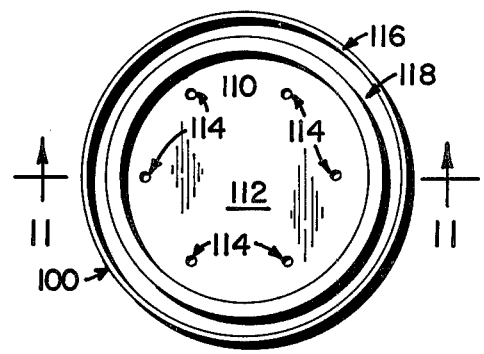
FIG. 11   FIG. 10
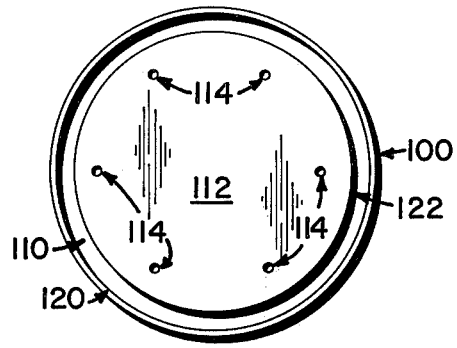
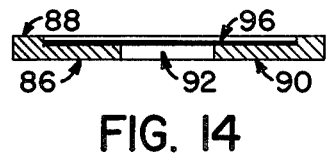
FIG. 12   FIG. 14
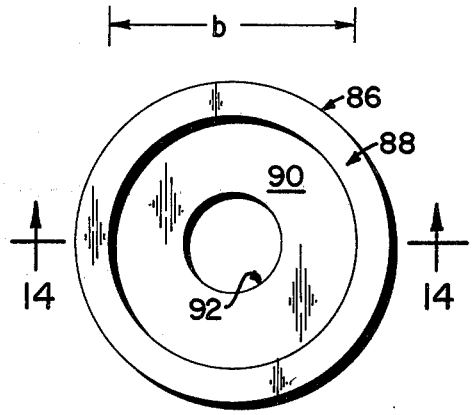
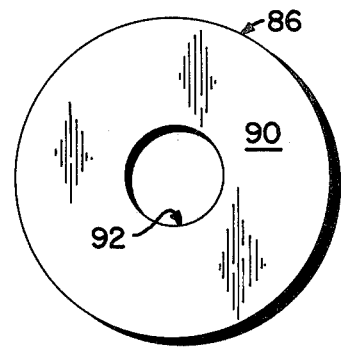
FIG. 13   FIG. 15

SIZE DISTRIBUTIONS OF TWO TYPICAL AEROSOLS DETERMINED BY THE IMPACTOR THAT IS THE SUBJECT OF THIS INVENTION.

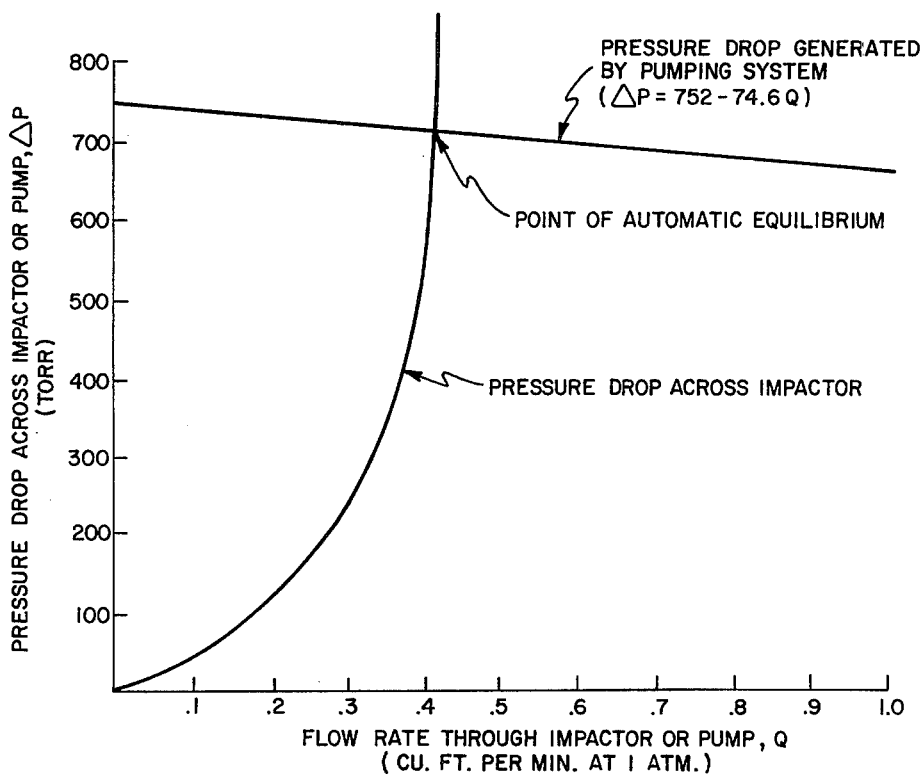
IMPACTOR AND PUMPING SYSTEM PERFORMANCE CURVES.
FIG. 28
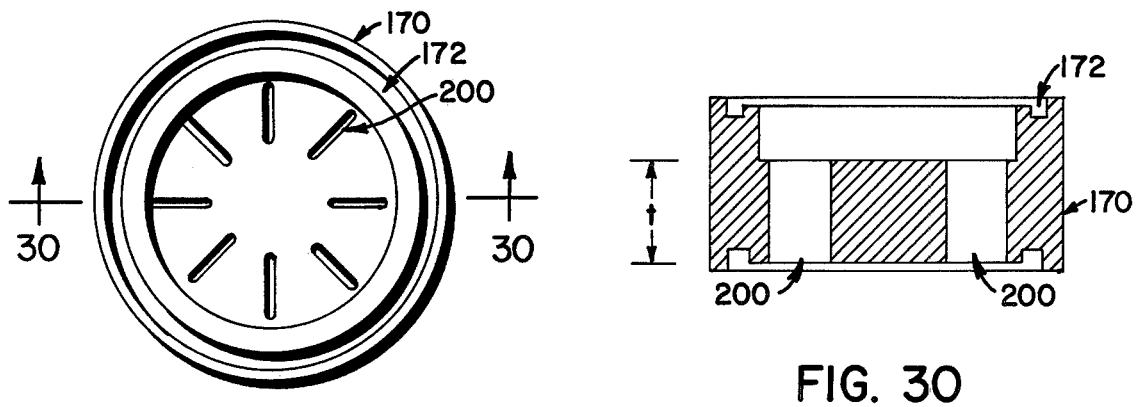
FIG. 29
FIG. 30

BOUNCELESS HIGH PRESSURE DROP CASCADE IMPACTOR AND A METHOD FOR DETERMINING PARTICLE SIZE DISTRIBUTION OF AN AEROSOL

This application is a continuation-in-part of my co-pending patent application, Ser. No. 464,158, and filing date of Apr. 25, 1974, now abandoned.

THE GENERAL BACKGROUND OF THE INVENTION

In the atmosphere around cities and industrial plants, there are many small particles of matter.

An aerosol may be defined as a group of solid particles or liquid particles suspended in a gaseous medium. The size range of these particles is generally between 10 nanometers and 100,000 nanometers in diameter. In an aerosol, the large particles account for most of the mass or weight of the aerosol. From observation, it appears that the particle sizes between 100 nanometers and 1000 nanometers cause the greatest health impairment and also cause the greatest decrease of visibility in the atmosphere.

Prior to this invention, there was no convenient means or method to measure the size distribution for particles in the size range of 10 nanometers to 300 nanometers in the atmosphere. If the size of the particles in an atmosphere could be measured to 10 nanometers, it is reasonable to conclude that means and methods could be found to control these fine particles in the atmosphere and to remove these fine particles so as to lessen the danger to the health.

Examples of pollutants and particulate matter in the atmosphere are the effluent from a plant burning coal, effluent from an aluminum reduction plant, and the general particulate matter in the atmosphere.

The effluent from a plant for burning coal comprises particulate matter ranging in size, as determined by a cascade impactor prior to this invention, of particles having a diameter in the range of 300 nanometers to 10,000 nanometers. The cascade impactors prior to this invention were not capable of measuring the particle size to a diameter less than 300 nanometers. The effluent from a coal burning plant comprises a, relatively, wide reeange of particle sizes. The larger particles of the atmosphere, relatively, close to the coal burning plant while the smaller particles will settle out of the atmosphere at a greater distance from a coal burning plant. And, the smallest particles in the effluent will not settle out from the atmosphere but will be washed out of the atmosphere by rain and snow and the like. It is my understanding that, the particle sizes between 50 nanometers and 1000 nanometers pose the greatest problems to health. For example, at the present time, it is believed that the particles having a diameter in the range of 50 nanometers to 1000 nanometers pose the greatest health hazard and the particles having a diameter in the range of 100 nanometers pose the greatest bisibility problems. The particulate matter in the effluent from a coal burning plant poses problems with respect to determining the size of the particulate matter and also in removing the particulate matter from the effluent. At the present time, one of the biggest problems is the determination of the size of the particulate matter in the effluent.

Another example is the size of the particulate matter in the effluent from an aluminum reduction plant. As is well known, in an aluminum reduction plant there are used electrodes. The electrodes are made from a paste of carbon particles in a hydrocarbon matrix. For example, the anode may be formed in the Soderberg process by continually adding paste and letting the hydrocarbon bake or heat and cook to form an anode. In the formation of the anode, there is given off a large amount of hydrocarbons. Or, the anode may be formed in a separate facility so as to be a prebaked anode and then inserted into the potline for making the molten aluminum. In the facility for prebaking the anode, there is also given off a large amount of hydrocarbon. The hydrocarbons are given off into the atmosphere and, because of a nucleation process taking place in the atmosphere, are condensed to form a haze, such as a typical blue haze. At the aluminum reduction plant at Tacoma, Washington, the effluent from the plant was measured by a cascade impactor, prior to the cascade impactor of this invention, and the particle size ranged from a diameter of 300 nanometers to 10,000 nanometers. There is scientific reason to believe that in the effluent from the aluminum reduction plant, there were many particles of a diameter of less than 300 nanometers, but the capacity of the prior cascade impactor was not sufficient to capture and weigh a particle size less than 300 nanometers. The comments with respect to the particle size distribution in the effluent from the coal burning plant are applicable to the particle size distribution in the effluent from the aluminum reduction plant with respect to posing a health hazard and to posing a visibility hazard. Further, it is known that in the effluent from a Soderberg aluminum reduction plant that the effluent contains 3-, 4-benzopyrene which is a carcinogen and hazardous to the health of individuals.

In Seattle, Washington area, the particle size distribution in the atmosphere for Mar. 17, 18 and 19, 1966, was determined by capturing the particles by means of a thermal precipitator on a glass plate and, then by means of an electron microscope, determining the size of the particles captured. The size distribution ranged from 10 nanometers to 1000 nanometers. This is a typical particle size range for aerosols generated in the atmosphere.

The small particles in an aerosol may be the result of a comminution process whereby erosion reduces the size of a particle to form the smaller particle. An example is the grinding of metal, the rubbing together of solid material, the blowing of wind on rock, and many crushing and grinding operation that are common in industry. Another way of forming the small particles is the atmosphere is by a nucleation process whereby gases can condense or react to form tiny liquid or solid particles. After these particles have nucleated, they grow by coalescing with one another and/or by gas condensing on the particles to form larger particles. As a generalization, particles formed by the nucleation process are less than about 300 nanometers in diameter and particles formed by the comminution process are greater than about 300 nanometers in diameter.

There are means and methods for measuring particles having a diameter less than 1000 nanometers. One of these is the Aiken Counter which is capable of measuring the number of particles having a size less than 100 nanometers. The size of the particle itself is not measured by the Aiken Counter but the number of particles below 100 nanometers in diameter are measured. Also, there is a question in regard to the interpretation of the results of the Aiken Counter. This introduces a question of the reliability of the results of the Aiken Counter.

Another means is the diffusion cell for measuring the particle size. In the use of the diffusion cell, it is necessary to have an individual cell for each range of particle size. This means that the diffusion cell process is an expensive process and also a tedious process to use. With the diffusion cell, it is possible to measure a particle size in the range of about 10 nanometers in diameter.

Another means is the combination of a thermal precipitator and an electron microscope wherein the thermal precipitator captures all the particles and with the aid of the electron microscope the size of the captured particles can be determined. The means for capturing and determining the size of the particles is expensive and the process is a slow process.

Another means is a cascade impactor. In a cascade impactor, there are a number of stages, each stage comprised of a jet plate and a collection plate. As the aerosol-laden gas passes through the impactor, the gas is caused to pass through each jet plate and impinge on the corresponding collection plate. The gas velocity in each jet stage is higher than the velocity in the preceding stage. As the gas passes from stage to stage, each collection plate collects a smaller size range of particles than was collected by the preceding stage. The collection plates are weighed before and after the sampling period to determined the weight collected by each stage. In using a cascade impactor, the impactor is calibrated so that the particle size range captured on each plate is known. It is then possible, by means of the weight of the particles captured on the plate and the particle size range, to state the percent of particles by weight in a given stage or on a given plate. One of the disadvantages of the prior cascade impactors has been that a hard particle in an aerosol, such as fly ash from a coal burning plant, will bounce on the plate. A further disadvantage of a cascade impactor, prior to this invention, has been that a particle size less than 200 nm in diameter has not been captured except for research models operating at very low inlet pressure. A particle having a diameter less than 200 nm flows through the cascade impactor and is not captured for measurement and determination. In certain instances, particles having a size less than 200 nm have flowed through the cascade impactor and have been captured on a filter. The filter has been weighed so it is possible to know the aggregate weight of the particles having a diameter less than 200 nm but it has not been possible to determine the size of these particles.

THE GENERAL DESCRIPTION OF THE INVENTION

The invention is a cascade impactor comprising a plurality of collector plates positioned between jet plates. A gas containing solids and/or liquids, an aerosol, is drawn into the impactor and certain of these solids and/or liquids impact upon a collector plate and are entrapped on the collector plate.

The velocity of the gas containing the liquid and/or solid increases in flowing through the impactor. Initially, the velocity of gas is, relatively, slow so that the larger particles contact the collector plate and stay on the collector plate. Then, the gas flows through a jet plate and the velocity increases slightly, and the particles in the gas contact the next collector plate and some of these particles remain on the next collector plate. Now, this process is repeated many times in going from a jet plate to the next succeeding collector plate. In going from the preceding jet plate to the succeeding jet plate, the velocity increases and the particles collected on the collector plate decrease in size. As is readily appreciated, the series of successive collector plates function to collect smaller size particles.

The velocity of the gas and particles depend upon the hole size and the number of holes in the jet plate. The succeeding jet plates have smaller hole sizes than the preceding jet plates until the minimum practical hole size is reached. Then, the hole size remains the same for a number of jet plates. For the last one or two or three jet plates, the hole size may increase to accomodate the larger volume of gas of the latter stages, which results from gas expansion through the impactor.

The collector plates comprise a substrate or a substrate liner. The substrate or substrate line may be foil such as aluminum foil or may be a plastic. The substrate liner is chosen so that the tare weight of the liner is as small as, reasonably, possible. It is called to the attention of the reader that the weight of particles collected on the substrate liner is, relatively, small and the weight of the substrate liner should be small. Also, the substrate liner is weighed before the sample is taken and weighed after the sample is taken so as to determine the weight of the sample. For example, the substrate liner is weighed on a micro-balance capable of measuring to as small as 1 microgram. The substrate liner may weigh in the range of 100 milligrams. From this, it is seen that it is desirable to have the substrate liner be of a low weight.

There is terminology used with respect to the cascade impactor known as $d_{50}$ which symbolizes the diameter at which 50 percent of the particles are captured on a given stage or on a given collector plate. The analyzer, by knowing the weight of the particles captured and the $d_{50}$ value for that particular collector plate, and then the $d_{50}$ values for all the collector plates, can make a particle size distribution calculation.

Cascade impactors prior to this invention have had a lower size limit of about 200 nanometers. Also, in previous impactors, the hard particles and high-density particles have bounced off the collector plates. With this impactor, the $d_{50}$ value on the last stage indicates a diameter of 40 nanometers. The smallest particle capable of being collected on this impactor is in the range of a Stokes diameter of 10 nanometers, wherein a Stokes diameter represents the real diameter times the square root of the density of the particle being collected on the collector plate. From this, it is to be realized that the Stokes diameter of a high-density particle is greater than the real diameter of the high-density particle and thus the Stokes diameter of a particle having a density less than the density of water is greater than the real diameter. For example, fly ash from a coal burning plant has a relatively high density of about 2.5. The real diameter of the fly ash may be in the range of 15 nanometers, but the Stokes diameter may be in the range of about 24 nanometers.

Further, with this invention, I have tried to eliminate the bounce of hard and high-density particles from the collector plate. This, I believe, is an accomplishment which has not been realized with other cascade impactors. To overcome the bounce off of the collector plates, other researches have coated the collector plates with an absorption material such as a grease or an oil or a mat such as a fiberglass mat. The use of such materials is messy and time consuming and with a grease or an oil there results a weight inaccuracy due to some vaporization of the grease and oil from the collector plate. With fiberglass, there is an even more serious problem as some of the fiberglass will flake off when being handled, after the particles have been collected on the collector plate and cause weight inaccuracies or sill result in an inaccurate weight.

THE OBJECTS AND ADVANTAGES OF THE INVENTION

An object and advantage of this invention is to separate an aerosol into particle size distribution fractions by inertial means and not by electrical means such as condensation nuclei; a further object is to provide the teaching for making an impactor and which impactor needs to be calibrated only once and does not have to be calibrated each time it is employed or used; another object is to disclose an impactor which is a simple instrument to make; a further important object is to disclose an impactor which is a rugged instrument; another important object is to disclose an impactor which is a reliable instrument for determining particle size distribution in an aerosol and which particle size distribution can be repeated; another practical aspect of this invention is to provide an impactor which is, relatively, inexpensive to manufacture; a further important object is to provide an impactor whereby it is easy to train someone to use the impactor and it is not necessary to have a, highly, formally, educated person to use the impactor; an additional object is to provide an impactor which makes it possible to get a particle size distribution of an aerosol wherein the smallest size particle may have a Stokes diameter in the range of about 10 nm; an additional object is to provide an impactor whereby it is possible to get an accurate particle size distribution of the particles in an aerosol; a further important object is to provide an impactor whereby the impactor can be used in on-site testing of an aerosol to determine the particle size distribution and the impactor is portable and not limited to use as a research tool but can be used in the field as a practical operating tool; and, to provide an impactor whereby it is not necessary to use a medium such as oil or grease or a fiberglass mat on the collector plates for capturing and retaining the particles.

A further advantage of the impactor is the self-regulating feature which will be described later.

An example of the work that can be done by the impactor of this invention is illustrated in FIG. 27 which shows two curves of actual test data. One curve shows a size distribution for stack gas from a hog fuel boiler. The other curve shows a size distribution for the roof vent monitor gases from a Soderberg aluminum reduction plant. In both cases the analyses show considerable detail about the size distribution at particle diameters less than 1000 nanometers. By comparison, the data was recalculated to show the amount of information that would have been obtained from one of the cascade impactors previous to the one that is the subject of this invention. The Solid black circles on FIG. 27 are the points that would have been obtained by a previous impactor at sizes less than 1000 nanometers.

With the use of this impactor it has been possible to discover that the peak concentration of fine particulate (smaller than 2000 nanometers diameter) is invariably at 300 nanometers. So far as is known, this phenomena has not been observed before in industrial effluent stacks. Thus a new tool has been made available to scientists and others in the field of air pollution control. This tool will measure fine particulate sizes at the high concentrations that are encountered in industrial stacks, something that could not be done before.

These and other important objects and advantages of the invention will be more, particularly, brought forth upon reference to the accompanying drawings, the specific description of the invention, and the appended claims.

THE DRAWINGS

In the drawings:

FIG. 1 is a fragmentary side elevational view of a specific embodiment of this invention constructed in accordance with the teachings thereof;

FIG. 2 is an end view looking into the entrance of the impactor;

FIG. 3 is an end view looking into the exit of the impactor;

FIG. 4, taken on line 4—4 of FIG. 1, is a longitudinal cross-sectional view illustrating the details of construction of the impactor and by means of lines and arrows the flow pattern of the aerosol-laden gas through the impactor;

FIG. 5 is an inside view of the outlet head of the impactor and looking outwardly through said outlet head;

FIG. 6 is an inside view of the inlet head of the impactor and looking outwardly through said inlet head;

FIG. 7 is a top view of the impactor plate of Stage 1 of the impactor and looking into the inlet side of said impactor plate;

FIG. 8, taken on line 8—8 of FIG. 7, is a longitudinal cross-sectional view of said impactor plate;

FIG. 9 is a bottom view of the impactor plate of Stage 1 and is looking at the outlet side or the downstream side of said impactor plate;

FIG. 10 is an inside view looking at a typical jet plate such as used on Stage 2 and the like of the impactor and looking into the jet plate or the upstream side of the jet plate;

FIG. 11, taken on line 11—11 of FIG. 10, is a longitudinal cross-sectional view of said jet plate as used, for example, on Stage 2 of the impactor;

FIG. 12 is a plan view looking at the outlet side or the downstream side of a typical jet plate as used, for example, on Stage 2 of the impactor;

FIG. 13 is a view looking into a collector plate such as used on Stage 2 and the like of the impactor;

FIG. 14, taken on line 14—14 of FIG. 13, is a longitudinal cross-sectional view illustrating the collector plate and also the substrate placed on the collector plate for collecting the liquid and the colid in the aerosol-laden gas;

FIG. 15 is a view looking at the outlet or downstream side of the collector plate such as used on Stage 2 and the like of the impactor;

FIG. 16 is a view looking at the substrate placed on a collector plate and which substrate collects the liquid and the solid particles from the aerosol laden gas;

FIG. 17, taken on line 17—17 of FIG. 16, is a cross-sectional view of the substrate;

FIG. 18 is a view looking into a jet plate or looking into the upstream side of a jet plate, and which jet plate is positioned near the outlet end of the impactor, and illustrates the plurality of small holes in the jet plate;

FIG. 19 is a longitudinal cross-sectional view of a jet plate of FIG. 18, for a jet stage which has the minimum jet plate thickness (dimension t);

FIG. 20 is a view of the outlet side or the downstream side of the jet plate of FIG. 18;

FIG. 21 is a longitudinal cross-sectional view of a jet plate of FIG. 18, for a jet stage which has a very thick jet plate, for reasons which will be explained later;

Figure 27:
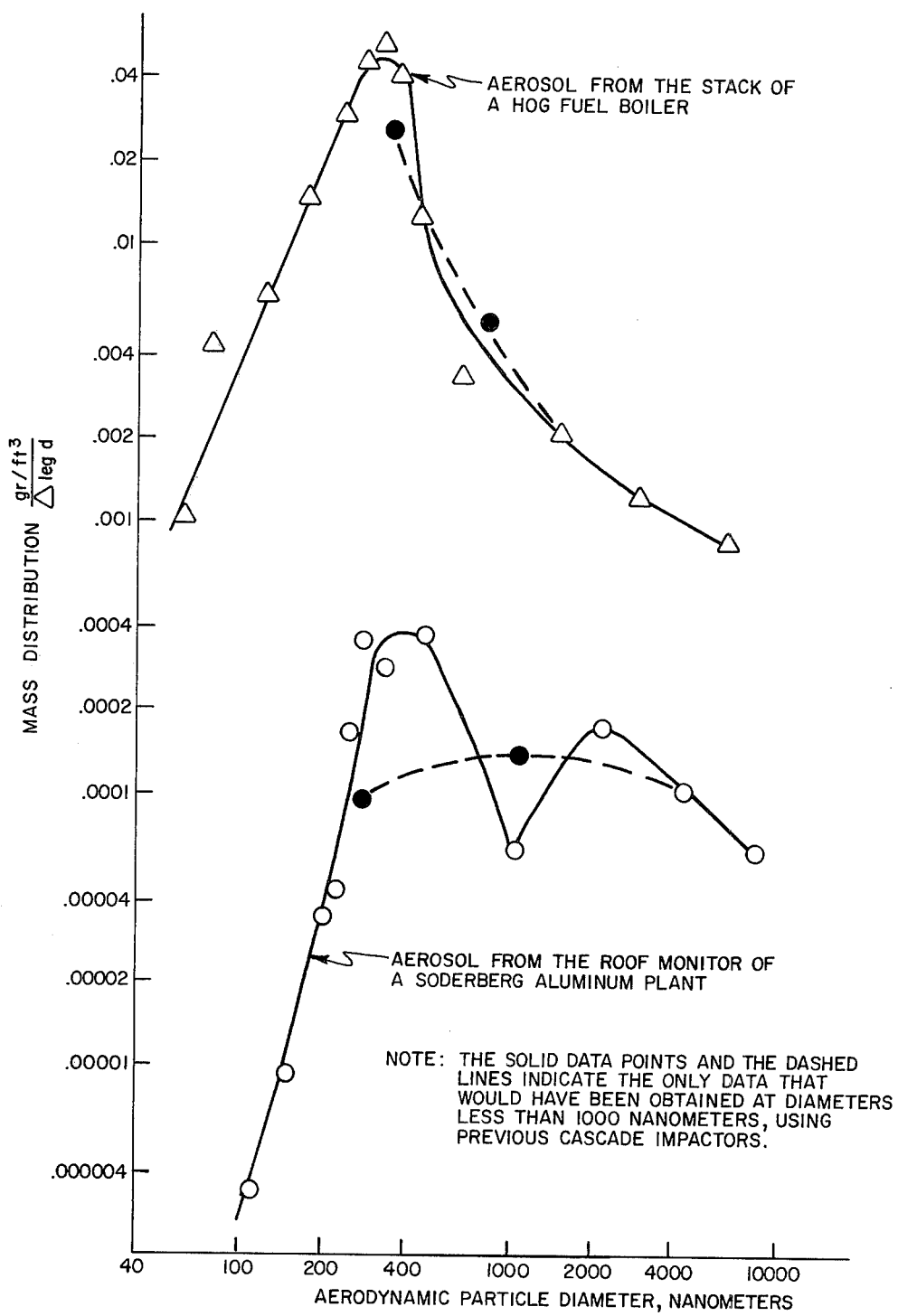

FIG. 27 is a graphical representation of data illustrated by open triangles and open circles and solid lines from two sized distribution determinations made with an impactor according to the teachings of this invention and with the solid black circles and the dashed lines to represent a calculation of the amount of data what would have been obtained in these tests if an impactor, other than the impactor according to this invention, and been used; and, FIG. 28 is a graphical representation of the pressure drop curves for the impactor and for the vacuum pumping system.

FIG. 29 is a drawing of the upstream face of a jet plate which employs the alternate configuration of slit jets.

FIG. 30 is a cross-sectional view of the slit jet plate along section 30—30.

THE DETAILED DESCRIPTION OF THE IMPACTOR

This cascade impactor is comprised of a series of stages. Each stage is comprised of a jet plate and a collector plate substrate. Each jet plate has one or more holes which direct the gas toward the corresponding collector plate. The collecting surface of each collector plate substrate is so positioned so as to be directly in the path of the stream or streams from the corresponding jet plate. When an aerosol-laden gas passes through the cascade impactor it goes through the first jet stage, thence is deflected off the first collector plate substrate, and passes through the second jet stage, and is deflected off the second collector plate substrate, and so on until the stream is deflected off the last collector plate and passes to the vacuum pump.

When a gas stream containing an aerosol particle is directed toward a flat plate, the particle will impinge on the plate and remain on the plate, or the particle will be swept aside by the gas stream, depending upon the size (and hence inertia) of the particle and the velocity of the gas stream. In the first jet stage, the velocity of the gas is low, and only the largest particles are captured on the first collector substrate.

The size of the jet holes and the number of jet holes are selected so that, in general, the velocity of the gas in each jet stage is greater than the velocity of the gas in the preceding stage. Each collecting substrate, downstream from its respective jet stage, collects a fraction of the aerosol particles that is smaller in size (diameter) than the fraction captured by the preceding collecting substrate. Each collecting substrate is weighed before and after the sampling period, so that the weight of particles in each size fraction is determined. From these data, a particle size distribution is calculated. Note:

(In certain cases, the velocity of the gas in a jet plate will be less than the velocity of the gas in the preceding jet plate. However, the product of the gas velocity and the Cunningham slip correction factor (that is, $V \times C$) for any stage will always be greater than said product for the preceding stage.).

It is to be realized that those particles having a particle size less that about 10 nm (or 5 nm in the case of dense particles), continue to flow through the impactor in the aerosol-laden gas. The particles having a particle size greater than about 10 nm will separate from the gas stream and be impacted on one of the collector plate substrates and be weighed for the size distribution analysis. More particularly, the first stage of the impactor will capture those particles in the gas stream having a particle size of about 10,000 nm or greater. Then, those particles in the range of about 10 nm particle size to about 10,000 nm particle size will be captured on the other collector plates so as to separate the particles according to their size range on the other collector plates or substrates so as to realize said particle size distribution analysis by weight.

Figure 1:
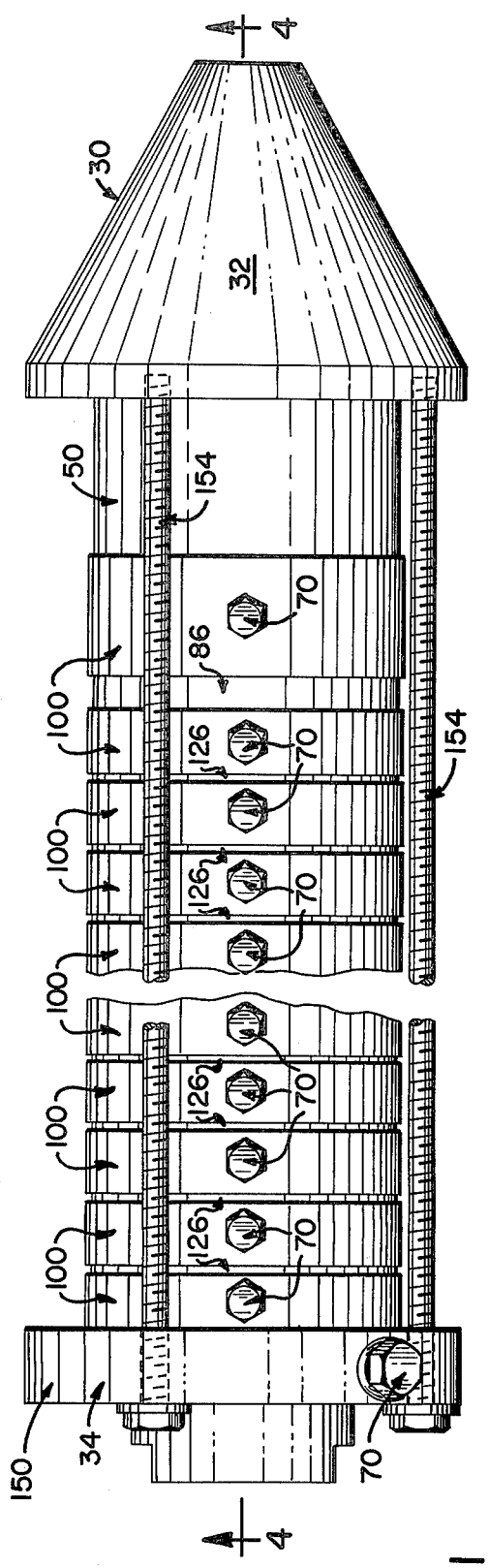
Figure 3:
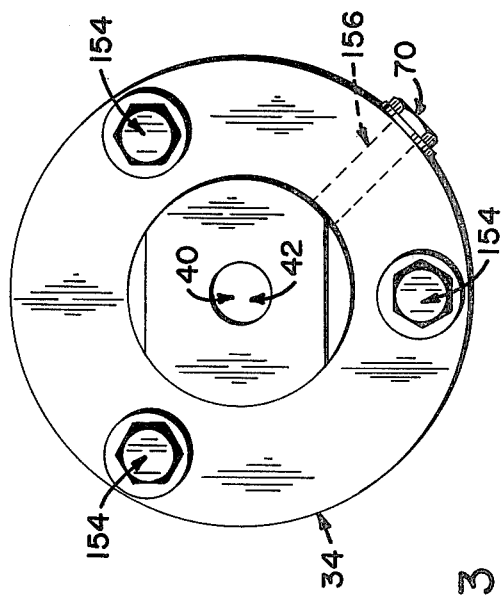
Figure 2:
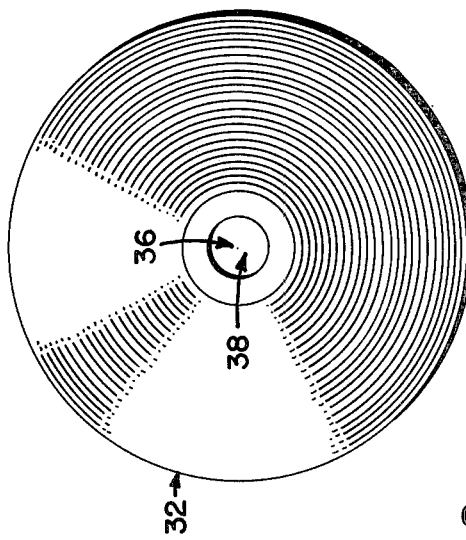

In FIG. 1, there is illustrated in a side elevational view, the impactor 30 having an entrance nozzle 32 which is also the first jet stage and an exit fitting 34.

Figure 4:
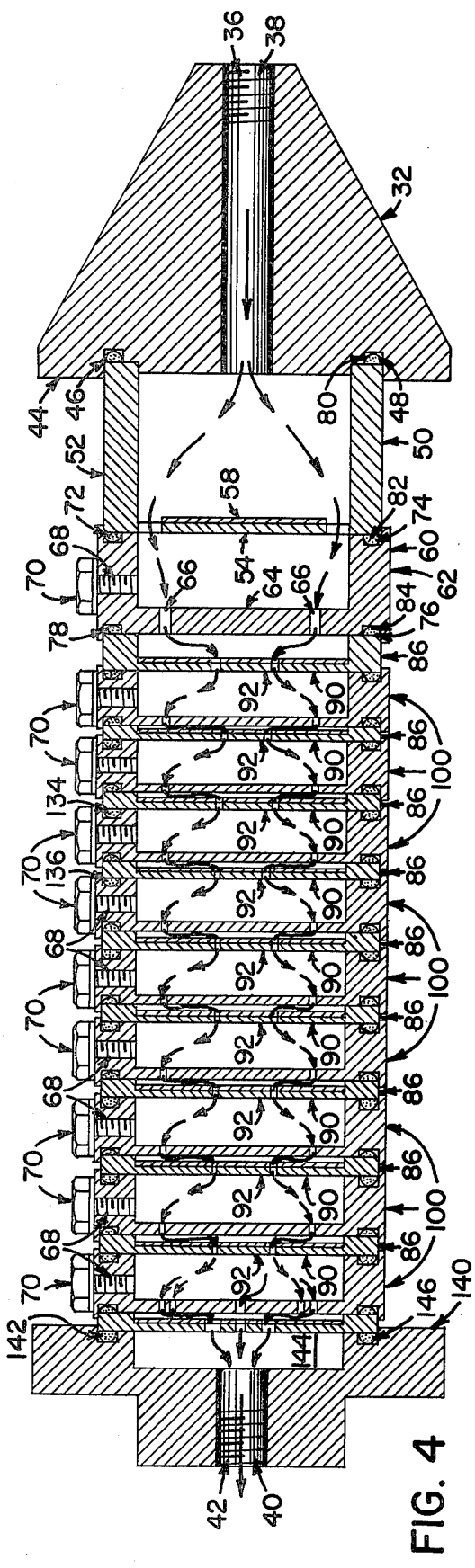
Figure 6:
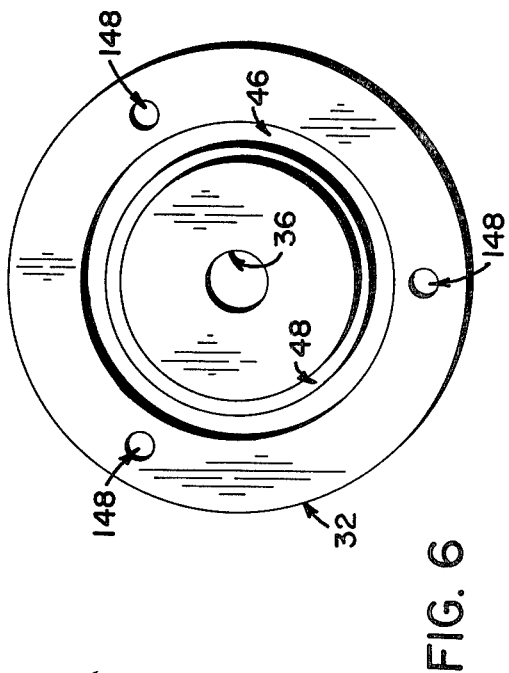

In FIG. 4, it is seen that the entrance nozzle has longitudinal passageway 36 which is tapped at 38 at its outer end.

In FIG. 4, it is seen that the exit fitting 34 has longitudinal passageway 40 which is tapped at 42 on its outer end.

The entrance nozzle 32 has a back side 44. In the back side 44 there is a circular groove 46. Further, in the back side 44 and connecting with the circular groove 46 is a circular groove 48.

The impactor 30 comprises a first collector unit 50 having cylindrical side walls 52 and a first collector plate 54. In FIG. 7 there is illustrated a view looking into the first collector unit 50 and the first collector plate 54. In FIG. 9, there is a view looking at the exit side of the first collector unit 50 and the first collector plate 54. In FIGS. 7, 8 and 9, it is seen that around the periphery of the plate 54, there are four passageways 56.

In FIGS. 4, 7 and 8, there is shown a thin substrate 58 overlying the upstream face of the plate for collecting the particulate matter carried by the aerosol. The substrate 58 may be aluminum or a plastic or other suitable material.

In FIG. 4, there is illustrated a second jet stage 60 having cylindrical side wall 62 and a second plate 64. In the second plate 64 are a number of passageways 66 to accelerate the flow of gas through the second plate 64 for causing a certain fraction of the particulate matter in the gas to deposit on the next succeeding collector plate. In side wall 62, there is a tapped opening 68. The tapped opening 68 is for receiving the inlet to a pressure sensitive device. When the pressure sensitive device is not connected to the impactor 30, there is a bolt 70 in the tapped opening 68. The second jet plate 60 has on its inlet side of the side wall 62 a surface 72 and in the surface 72 is a circular groove 74. Also, on the outlet side, there is a surface 76 and in the surface 76 is a circular groove 78.

In FIG. 4, it is seen that in the circular groove 48 in the entrance nozzle 32 there is an O-ring 80. In the groove 74, there is an O-ring 82 and in the groove 78, there is an O-ring 84.

In FIG. 4, it is seen that there is a second collector unit 86 having a circular side wall 88 and a collector plate 90. In the collector plate 90, there is a central passageway 92. It is to be realized that in the second collector plate 86 and on the upstream side of the collector plate 90, there is a thin substrate 96 for collecting the particulate matter in the gas stream and which particulate matter will separate as a fraction onto the thin substrate 96. More, particularly, in FIGS. 16 and 17, there is illustrated the thin substrate 96 of a generally cylindrical configuration and having a central passageway 98 to allow the gas to flow through the substrate. The central passageway 98 in the thin substrate 96 will be aligned with the central passageway 92 in the collector plate 90. Again, the thin substrate 96 may be aluminum or plastic or other suitable material. It is to be recalled that one of the reasons for using the thin substrate 96 is the weighing of the thin substrate before it is used to collect particulate matter so as to establish a tare weight and then to weigh the substrate with the particulate matter to determine the weight of the particulate matter. With the analytical equipment used, it is desirable to have the thin substrate weigh as little as possible so as to have as small a tare weight as possible. In other words, a light weight substrate increases the sensitivity of the balance so as to be able to secure a more accurate weight of the particulate matter.

When the impactor is used in any position other than the entrance nozzle pointing up, there is a problem of keeping the substrate foil or plastic film 96 in position on the upstream face of the collector plate 90. If the foil contacts the downstream face of the jet plate 100 or 170, proper impaction and separation of particles cannot take place, because there is not enough clearance distance between the downstream face of the jet plate and the impaction surface. Neither an adhesive nor an oily or sticky substance may be used to secure the substrate 96 to the upstream face of the collector plate 90, because the substance used would interfere with the weighing of the substrate before and after the test run.

Figure 16:
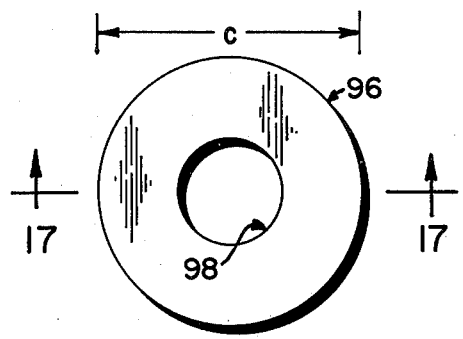
Figure 17:

The innovative feature used in this invention to secure the substrate foil 96 onto the collector plate 90 is to ram the substrate foil 96 onto the collector plate 90 using an interference fit and into the collector unit 86. In other words, the diameter of the substrate foil, dimension "c" in FIG. 16, is slightly greater than the inside diameter of the collector plate, dimension "b" in FIG. 13, collector plate 90, and the collector unit 86. In practice, if dimension "c" is about 0.005 inches greater than dimension "b", the interference fit is satisfactory.

To use this principle, a tool, viz, a ram, is made which is merely a solid metal cylinder whose diameter is about 0.005 inches less than dimension "b". After the substrate has been weighed and before the test has been run, the tool is used to ram the substrate 96 onto the collector plate 90 such that the substrate is held against the upstream face of the collector plate 90 and in the collector unit 86. In this manner the substrate is held firmly in the proper relation to the collector plate 90 throughout the test, regardless of the position of the impactor.

In FIG. 4, it is seen that the length of the passageway 36 and the entrance nozzle 32 is, relatively, long and that the length of the side wall 52 in the first collector unit 86 is relatively long. Further the length of the side wall 62 in the second jet stage is not as long as the length of the passageway 36 in the entrance nozzle 32, but that the length of the side wall 62 is longer than for succeeding jet stages. Likewise, the length of the side wall 88 in the second collector unit 86 is not as long as the length of the wide wall 52 in the first collector unit 50 but is longer than the side walls in the succeeding collector units. One of the reasons for the longer side walls and passageways in the first few jet stages and collector units is a safety factor to try to ensure the heavier particles in the aerosol will not be prematurely impacted onto a collector plate or onto the walls of the impactor.

After the first few jet stages and collector units, some of the collector units may have the same wall length. However, in the case where some of the jet stages must be made thick, as shown in FIG. 21, the wall lengths may increase as required by the dimensions imposed by the "step-by-step design process."

The length of the side wall of the collector unit and, the distance between the downstream face of the jet plate and the upstream face of the next succeeding collector plate cannot be less than the diameter of the hole of the jet plate. From experience, I have selected this distance to be at least three times the diameter of one hole of the jet plate. It is to be realized that the jet stage, after the first few jet plates, may have the same wall length but have different numbers of passageways or jet holes. Further, the diameters of the holes in the jet plates may be different. For example, in the middle portion of the impactor 30, the diameters of the holes in the jet plates may decrease for the succeeding jet plates. Then, there is realized a terminal diameter for the holes in the jet plates as it is not prectical to make a hole any smaller than a certain size in the jet plate. This limitation is dictated by a practical cost limitation for the making of the small holes in the jet plate. For example, the diameter of the small holes in the jet plate may be 0.01 inches. For certain jet plates, in the latter stages of the impactor 30, there may be a large number of these small holes. It may be possible to make holes smaller than 0.01 inches in diameter, but then the number of these holes would be large. The cost of making the holes would be, correspondingly, large. Therefore, from a practical standpoint, the diameter of the holes in the jet plates will be not less than 0.01 inches. From a theoretical standpoint, the holes in the jet plate can be less than 0.01 inches.

In a typical impactor 30, the number of jet plates will be, approximately, 17 plates. In certain instances, the number of collector plates may be less than 17 while in other instances, the number of collector plates may be much more than 17, such as 30 collector plates. The number of collector plates will be dependent upon the fraction to be separated and the type of material which is being fractionated. In general, the design for a soft plastic aerosol would not require as many collector plates while the design for a hard, dense aerosol would require, relatively, a large number of collector plates.

In FIG. 4, there is illustrated a jet stage 100. Also, see FIGS. 10, 11, and 12. The jet stage 100 may be considered to be a typical jet stage having a circular side wall 110 and a bottom jet plate 112. In the bottom jet plate 112 are a number of holes or passagewyas 114. The side wall 110 has an inlet face 116 with a circular groove 118 in the inlet face 116. Also, the side wall 110 has an outlet face 120 with a circular groove 122.

The side wall 110 is a tapped passageway 124 for receiving a tap to a pressure sensitive device to indicate pressure. In the tapped passageway 124, when it is not attached to the pressure sensitive device, is the bolt 70.

Again, it is to be realized that the number of holes or passageways 114 and the diameter of these passageways 114 can vary from jet plate to jet plate depending upon the fraction to be separated. A typical collector unit 86 is illustrated in FIGS. 4, 13, 14 and 15. The collector unit 86 comprises a side wall 88 and a bottom collector plate 90 with the hole or passageway 92. There is positioned on the upstream side of the collector plate 86, the substrate 96 having the hole or passageway 98 aligned with the hole or passageway 92.

In FIG. 4, it is seen that in the circular groove 118, there is positioned an O-ring 134 and in the circular groove 122, there is positioned an O-ring 136.

Figure 5:
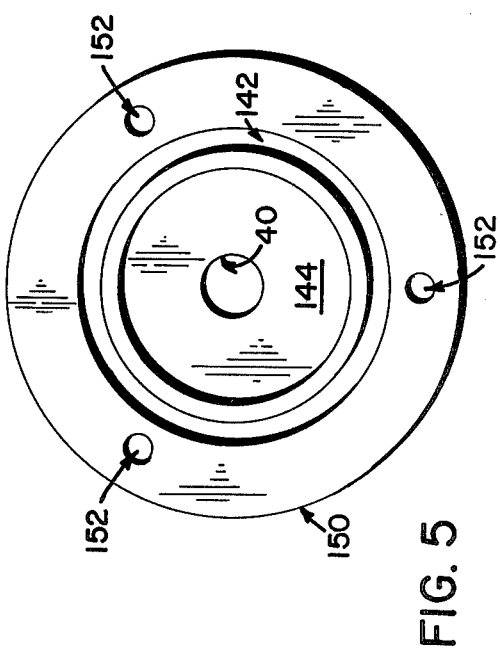

In FIGS. 4 and 5, it is seen that the exit fitting 34 has an upstream face 140 and in the upstream face 140 is a circular groove 142. Also, the central portion of the exit fitting 34 is recessed at 144. In FIG. 4, it is seen that in the circular groove 142, there is positioned an O-ring 146.

In the face 44 of the entrance nozzle 32, there are three drilled, tapped passageways 148.

The exit fitting 34 may be considered to have a circular shoulder 150 and in the circular shoulder 150 are three passageways 152 which can be aligned with the passageways 148 in the entrance nozzle 32. Three long bolts 154 may pass through the passageways 152 and be screwed into the tapped holes 148 so as to squeeze together the jet stages and the collectors units to make gastight seals in conjunction with the o-rings between the collector units and the jet stages.

Further, in the exit fitting 34, there is a drilled, tapped passageway 156 which is used as a pressure tap. When 156 is not used as a pressure tap, a bolt 70 is screwed into this drilled, tapped passageway 156.

The tapped passageway 40 on the exit fitting 34 is connected to a vacuum pump to cause the aerosol laden gas to flow through the impactor so as to have fractionation of the particulate matter in the aerosol-laden gas. Further, in designing the impactor, it is desirable to know the capacity of the pump for causing the flow of the gas through the impactor. It is desirable to know the capacity of the pump as a function of the downstream pressure of the impactor. By knowing this, it is possible to know the pump capacity and the minimum size of particulate matter which can be captured by the impactor.

In the entrance nozzle 32, the tapped passageway 36 is designed to be connected to various inlet tubes so as to achieve isokinetic flow of the aerosol-laden gas at the velocity of the gas stream undergoing tests or being sampled.

The impactor 30 may be used in various positions. For example, the impactor 30 may be used in a horizontal position or it may be used in a vertical position with the entrance nozzle 32 pointed into the downwardly flowing gas stream or the impactor 30 may be used in a vertical position with the entrance nozzle 32 pointed in the direction of the upwardly flowing gas stream. Further, in sampling a gas stream, the entrance nozzle 32 is directed into the flowing gas stream so as to sample the gas stream without disturbing the particle size distribution before it gets to the impactor.

Figure 18:
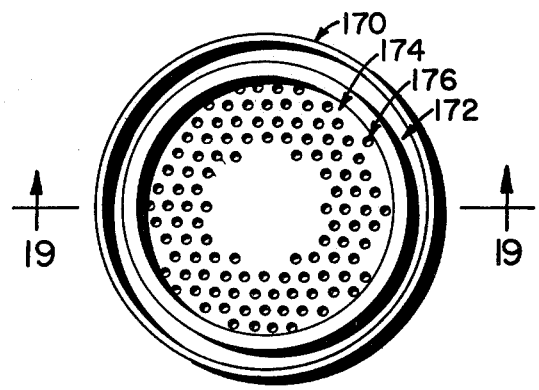
Figure 19:
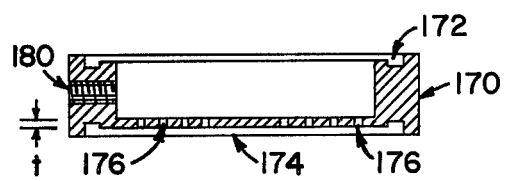
Figure 20:
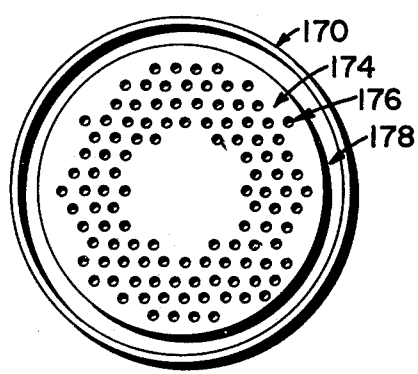

In FIGS. 18, 19 and 20 there is illustrated a jet stage 170. In FIG. 18, a view looking into the inlet side of the jet stage, it is seen that there is a recess 172 for receiving a sealing means such as an O-ring. There is a jet plate 174. In the jet plate 174 are a number of holes or passageways 176. The holes or passageways 176 are positioned in an equilateral triangle arrangement.

In FIG. 20, a view looking at the outlet side of the jet stage and the downstream side of the jet plate 174, it is seen that there is a recess 178 for receiving a sealing means or an O-ring.

In FIG. 19, a lateral cross-sectional view taken on line 19—19 of FIG. 18, it is seen that in the shoulder 179 of the jet stage 170 there is a drilled tapped passageway 180 for receiving a pressure tube.

The jet plate 170 comprises a large number of very small holes such as 1/100th of an inch in diameter.

From the foregoing, it is seen that I have provided a cascade impactor which makes it possible to sample a gas containing particulates or an aerosol. In sampling the gas or the aerosol, there is used the upstream stamospheric pressure which is in the range of about one atmosphere of pressure or about 760 millimeters of mercury at a temperature of 32° F. It is possible to sample a gas or an aerosol at a pressure much less than one atmosphere of pressure such as a pressure of 40 Torr or 15 Torr. These low pressures of 40 Torr and 15 Torr are realized at high altitudes and at other places. A Torr is a pressure of one millimeter of mercury. When the upstream pressure is at atmospheric pressure, then with my cascade impactor, it is possible to have a downstream pressure of about 40 Torr.

It is to be emphasized that the pumping system employed with my cascade impactor is important. For a portable cascade impactor and for a portable pumping system, it is possible to sample a particle size having a Stokes (Aerodynamic) diameter of about 40 nanometers, or as small as 10 nanometers real diameter for particles of specific gravity equal 3.0. With a more elaborate pumping system, which is not portable, viz., cannot be carried by one man, it is possible to sample a particle size having a Stokes diameter as small as 10 nanometers. It is to be realized that for a dense material or a dense substance a Stokes diameter of 10 nanometers may be a real diameter of as small as about 2 nanometers. For example, a gold particle having a Stokes diameter of about 10 nanometers may have an actual diameter of 2 nanometers or less. The upper reasonable limit for particulate matter to be sampled in a cascade impactor is at a $d_{50}$ of about 10,000 nanometers. This upper reasonable limit is based on the fact that for particle sizes larger than the upper limit it is extremely difficult to obtain a representative sample of the aerosol.

A novel feature of this invention is that the impactor is designed to exactly match the flow characteristics of a given preselected pumping system. In actual practice, the first thing that is done is to determine the pressure drop, P, vs. flow, Q, for the vacuum pumping system selected. See the upper curve in FIG. 28, for a typical such curve.

Then, using the step-by-step design method, the impactor is designed so that it will operate at design capacity merely by connecting a vacuum hose between the exit of the impactor and the inlet of the vacuum pumping system, and turning on the vacuum pumping system.

The impactor instantly achieves automatic equilibrium of flow at the design flow rate without need for manual regulation. The reason for instant self-regulation is seen when one examines the Pressure Drop Across Impactor Pump $\Delta P_{tot}$ vs Flow Rate Through Impactor Pump, Q.

Referring again to FIG. 28, the total pressure drop across the impactor, $P_{tot}$, increases very rapidly with the increasing flow rate. When the total pressure across the impactor, $\Delta P_{tot}$, equals the pressure drop generated by the vacuum pumping system, $\Delta P_{pump}$, the flow rate instantly stabilizes with the design flow rate and within the impactor achieves design velocities and design particle separation.

There are two important advantages that accure from this self-regulation feature, namely, (1) operation of the impactor is very simple, requiring only to turn the switch on and off, and (2) simplicity of design and operation leads to reliability.

The impactor described in the previous pages is the preferred embodiment of this invention. In fact, a working model of the invention, as described, has been built and tested in actual field conditions. However, other configurations could be designed and constructed which would use the teachings of this invention. In particular, let us consider the passage through which the gas flows from the collector plate surface of one stage to the upstream face of the jet plate in the next succeeding stage. This passage must be one having a low, that is, negligible, resistance to the flow of the gas. The preferred embodiment uses a circular hole 92 in the central part of the collector plate 90 to accomplish this purpose. Some other impactors described in the literature employ collector plates in which the gas flows from the collector plate to the next jet plate through passages around the periphery of the collector plate. FIGS. 7, 9 and illustrate a collection plate using the latter configuration. The point being made is that the teachings of this invention could be utilized with either center holes or peripheral slots in the collector plates, or indeed still other configurations.

In the terminology there is a reference to $d_{m(j-1)}$. The term "j" is an enumerator which refers to the stage of the impactor under consideration. The term (j−1) refers to the stage immediately upstream from the stage of the impactor under consideration. The term "d" is the diameter of particle being captured on a given stage. The term "m" is the percent of particles captured on a given stage. Thus, for instance, $d_{98(j-1)}$, refers to the diameter of particle, 98 percent of which will be captured on the collector plate of the stage immediately upstream from the stage of the impactor under consideration considered.

THE THEORY AND DESCRIPTION OF DESIGN PROCESS AND IMPACTOR OPERATION

The essence of the design of any round-hole cascade impactor is the selection of the diameter of jet holes and number of jet holes in each stage of the impactor so as to achieve the particle separation that is desired, that is, to design the impactor so as to achieve the $d_{50}$ values that are desired. In the particular case of this invention, the essence of design is the selection of the diameter of the jet holes, the number of jet holes, and the thickness of the jet plate, to achieve the desired particle separation and to achieve this separation without particle bounce or reentrainment.

THE GENERAL THEORY OF CASCADE IMPACTORS

All modern cascade impactors are based on the Ranz and Wong relationship:

$$\psi = \frac{c\rho_p d^2 V}{18 Du}$$

These investigators found, theoretically and experimentally, that the probability of a particle of diameter "d", being carried in a jet stream directed toward a flat plate, would be impacted on said plate, depends upon the value of the impaction parameter, $\psi$. For example, if a particle has a fifty (50%) percent probability of being impacted (and captured) on a given collection plate, said particle diameter would be designated $d_{50}$, the corresponding value of the impaction parameter is called $\psi_{50}$. Various workers, including the inventor, have found that when a particle has a fifty (50%) percent probability of being captured on a given stage, then the value of $\psi_{50}$ falls between 0.12 and 0.17 (the exact value varies with different experimenters). The inventor has found that a value of $\psi_{50}$ equals 0.145 is appropriate and most nearly fits all of his experimental data. The inventor has also experimentally determined various other specific values of $\psi$, such as:

$\psi 95 = 0.192$ (value of $\psi$ when there is a 95% probability of capture of particle of diameter $d_{95}$)

$\psi 98 = 0.209$ (value of $\psi$ when there is a 98% probability of capture of particle of diameter $d_{98}$)

$\psi 100 = $(approximately) 0.245 (value of $\psi$ when there is a 100% probability of capture of particle of diameter $d_{100}$)

In practice, the value $\psi_{100}$ is a limiting value and (1) is very difficult to determine accurately, and (2) leads to unnecessarily conservative and cimbersome designs, as will be seen in the following discussion.

The terms of the above equation are found in the nomenclature section.

It is readily seen that if the value of $\psi_{50}$ is a constant and is known, then value of $d_{50}$ for the various stages of the impactor can be calculated, and a design predicted. Indeed, this is the method used for previous cascade impactors.

THE PRESSURE DROP AND TEMPERATURE DROP PREDICTION AS PART OF THE DESIGN METHOD

In previous impactors, the assumption was made that pressure drop through the impactor had a negligible effect upon the impaction process. This assumption is close enough to reality to be able to design impactors which can size particles as small as 300 nanometers in diameter. However, the Cunningham slip correction factor, C, changes rapidly with decreasing pressure when the $d_{50}$ values become less than 300 nanometers.

An innovative feature of this invention is the precise prediction of pressure drop and temperature drop across each jet stage. This precision in prediction of downstream pressures and temperatures make possible the design of the impactor that extends the lower limit of particle diameters that may be captured from the present 300 nanometers to about 40 nanometers aerodynamic diameter (as small as 10 nanometers real diameter for dense particles).

Pressure drop across a given stage, P, is calculated by modifying the classical orifice equation to apply to a plate with more than one orifice, and solving for pressure drop; thus:

$$\Delta P = \frac{(1.49) \, W^2 \, T \, (1 - (A_f/A_t)^2)}{C_v^2 \, A_t^2 \, Y^2 \, P}$$

All of the terms are defined in the nomenclature section of this specification. All of the terms in the right side of the above equation may be readily determined except the orifice coefficient, $C_v$. $C_v$ is a complex function of jet stream Reynolds number, $Re_j$, and of thickness-to-diameter ratio of the jet holes, t/D. The experimental-mathmatical method of determining $C_v$ is explained in detail in the "step-by-step design process".

Once the pressure drop and the downstream pressure for a given stage have been determined, the temperature drop and the downstream temperature are predicted by calculating the adiabatic expansion of a gas. The procedure for accomplishing this prediction is described in detail in the "step-by-step design process".

The accurate prediction of pressure drop and temperature drop makes possible the accurate prediction of conditions of impaction of particles with $d_{50}$ values as small as desired. There are two practical considerations to be considered in regard to the particle size and the particle size distribution. First, as the $d_{50}$ becomes smaller and smaller, it is necessary for the vacuum pumping system, which causes the gas to flow through the impactor, to pump larger and larger volumes of gas at lower and lower downstream pressures. Greater and greater pumping capacity is associated with greater weight, size and cost of the pumping mechanism. Usually, it is desired to be able to carry the pumping system to the testing site. Therefore, a compromise must be made between the smallest $d_{50}$ attainable, and size and portability and cost of the pumping system. A large pumping system with a high capacity is desirable but may not be protable and may not be usable at the site of the test.

The second limitation is that as the $d_{50}$ values become smaller, the mass to be weighed on each substrate becomes less. A factor to consider is the limit of sensitivity of available balances to weigh the particles that are collected. For the purpose of this invention, a Stokes (aerodynamic) diameter of 40 nanometers for the last stage is believed to be the practical limit, that is $d_{50}$ for the last stage equals 40 nanometers Stokes diameter (as small as 10 nanometers real diameter for dense particles).

THE THEORY OF BOUNCE PREVENTION

A particle will not bounce from a surface if the energy that is available to hold the particle to the surface is greater than the kenetic energy that is conserved by the particle during collision.

The energy that is available to hold the particle to the substrate surface is the surface energy between the particle and the substrate. This quantitly is very difficult to determine in absolute terms; however, this quantity is proportional to the surface area of the particle, that is, proportional to $\pi d^2$.

The kinetic energy that is conserved by a particle during collision is, likewise, difficult to determine. However, this quantity is proportional to the total kinetic energy of the particle in the gas stream, that is, proportional to $$\frac{\rho_p \, \pi d^3 \, V^2}{12}.$$

It follows that, if the kinetic energy of the particle is the gas stream, per unit area of the particle, does not exceed some threshold value, the particle will not bounce. This threshold value, is defined as the Nelson bounce parameter, $$\beta = \frac{\frac{\pi \rho_p d^3 V^2}{12}}{\pi d^2} = \frac{\pi_p d V^2}{12} \, (g/sec^2) = \text{bounce parameter}.$$

The inventor has found experimentally, that in the case of potassium sulfate aerosol directed toward an aluminum foil substrate, if the value of $\beta$ is less than 350 g/sec², the particles will bounce severly and unpredictably. Therefore, a principal teaching of this invention is to design an impactor, using Ranz and Wond theory to predict $d_{50}$ values, and at the same time to keep velocities of the various stages no greater than the threshold value of 62 which will cause bounce. It is recognized that this threshold value of $\beta$ will be specific and different for each combination of aerosol composition and substrate composition, for two reasons. Firstly, surface energy per unit area of particle is specific for each such combination. Secondly, the fraction of kinetic energy conserved is dependent upon the elasticity of particle and elesticity of the substrate. It is believed that the combination of potassium sulfate aerosol and aluminum substrate is one of the worst combinations that an investigator is likely to encounter as regards tendency to bounce. It follows that a value of $\beta = 350$ g/sec² would lead to a conservative design that would eliminate bounce for the vast majority of aerosol-substrate combinations.

In using this insight into bounce prevention, one first selects a diameter, d, which will not be presented to the stage in question. The smallest diameter that has no possibility of being presented to a stage is the $d_{100}$ diameter for the stage prior to the stage in question. Therefore, in designing the stage, the velocity should be no greater than that which will give a value of 350, for example, using the $d_{100}$ diameter for the stage prior to the stage in question, that is, $\beta$ should be no greater than $$\frac{\rho_p \, d_{100(j-1)} V^2}{12}.$$

There is one modification of this procedure; $d_{98}$ is substituted for $d_{100}$ in the above relationship, that is, the velocity is limited to that for which $\beta$ is not greater than $$\frac{\rho_p \, d_{98(j-1)} V^2}{12}.$$

This modification results in a design with fewer stages, at the cost of having a very few particles bounce. At the very worst, no particle that would be large enough to bounce would have no more than about a 0.75 percent probability of reaching the given plate. It is also probable that the value $d_{95}$ could be substituted for $d_{100}$, resulting in still fewer stages and a more compact design, but also at the additional risk of some bounce for hard particles.

THE ROLE OF VERY THICK JET PLATES IN BOUNCE PREVENTION

The above described theory has been used to design and construct an impactor with values of equal to or less that 350 g/sec$^2$. The design process dictated that the $d_{50}$ values, of stages between $d_{50}=400$ nanometers and $d_{50}=100$ nanometers be spaced much closer together than would otherwise be desired. This impactor had 15 stages whose $d_{50}$ diameters are as follows:

| Stage | $d_{50}$, nanometers |
| --- | --- |
| 1 | 16,000 |
| 2 | 7,400 |
| 3 | 4,000 |
| 4 | 1,900 |
| 5 | 910 |
| 6 | 420 |
| 7 | 290 |
| 8 | 250 |
| 9 | 230 |
| 10 | 200 |
| 11 | 170 |
| 12 | 130 |
| 13 | 91 |
| 14 | 59 |
| 15 | 45 |

Form the point of view of convenience of operation, the $d_{50}$ of each stage should be approximately one half of the $d_{50}$ of the state immediately upstream. Such an impactor should need only 9 stages to cover the same range of particle diameters.

Figure 21:
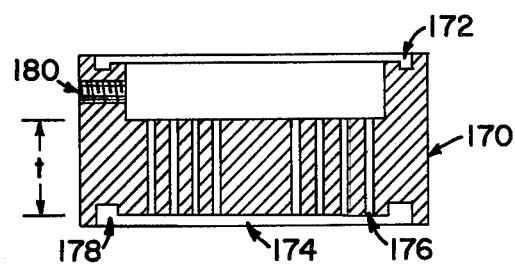
Figure 22:
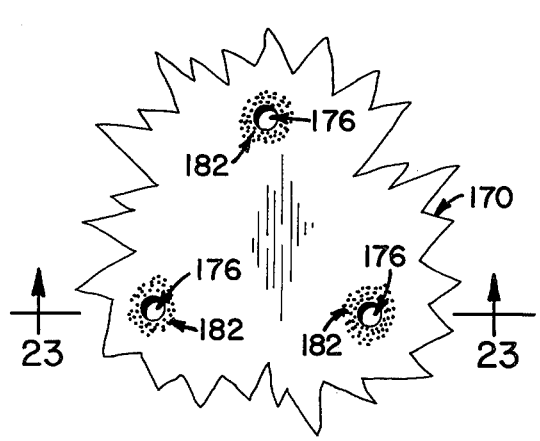
FIG. 22 is a magnified cut-away portion of FIG. 18 showing accumulation of particles on the jet plate when the jet plate has sharp-edged holes.
Figure 23:
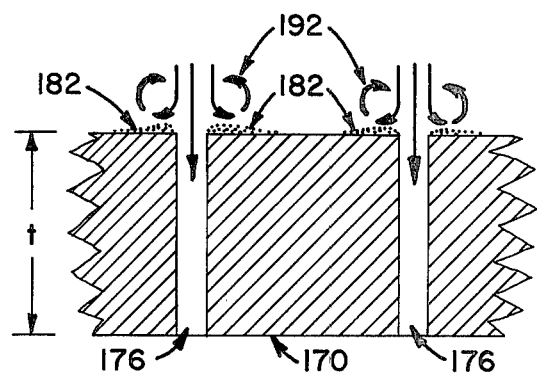
FIG. 23 is a cross-sectional view of FIG. 22 on line 23—23, showing the turbulent flow patterns of aerosol laden gas when the jet plate holes in the jet plate have square edges, and also shown are the accumulations of particles on the jet plate caused by the turbulence.
Figure 24:
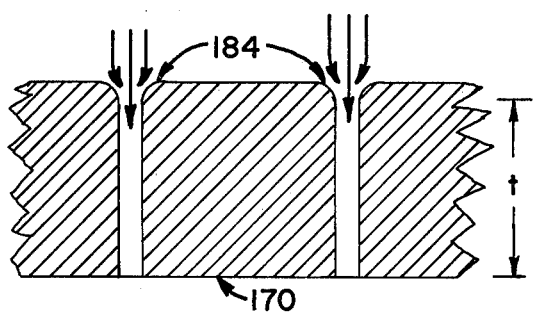
FIG. 24 is a cross-sectional view, similar to FIG. 23, except that the jet plate holes have rounded edges on the upstream side and with gas flow patterns illustrated with the reader's attention called to the lack of a collection of particles around the entrance to the holes and the difference in flow patterns between FIG. 23 and FIG. 24.

The first mentioned impactor had plates with a thickness dimention "t" in FIG. 19, of 0.050 inches for stages with the minimum jet hole diameter. If "t" is increased, as shown in FIG. 21, the pressure drop across the stage is increased without a corresponding increase in the velocity of the gas on the downstream side of the jet holes. To phrase it another way: (1) the increased length of travel of the gas through the jet holes causes the gas and the particles to be slowed down or decelerated by wall friction losses; (2) thereby achieving the low pressure and high Cunningham factors needed for impaction; (3) have velocities low enough to avoid bounce; and, (4) spacing the $d_{50}$ values far enough apart so that the whole range of particle sizes can be caught with about nine stages.

Thus, by using the variable of jet plate thickness, as well as the variable of number of holes in the jet plate, it becomes possible to obtain simultaneously (1) optimum desired spacing of $d_{50}$ values and (2) limitation of values of $\beta$ to avoid bounce. The detailed procedure for using this concept is incorporated in the "step-by-step design process".

It is of course obvious that it is impossible to protect the first stage from bounce by control of the $\beta$ parameter, because there is no control over the size of particles that might reach the stage. However, this is not usually a problem because for the first stage, the velocity needed to cause impaction of the largest particles is so low that the value of $\beta$ is low, that is, the velocity is controlled by considerations other than the value of $\beta$. Alternatively, the particles larger than about 10 microns or 10,000 nanometers can be removed by a precut cyclone just upstream from the first stage of the impactor.

A further consideration is that, since $\beta$ is proportional to the density of the particle, $\rho_p$, the greater the density of the particle, the more the bounce problem is aggravated. Most atmospheric aerosols have a density of about 1.0 g/cm$^3$ and even higher.

To design an impactor which will have the widest utility and freedom from bounce problems, one should select a value of $\rho_p$ which represents a worst case condition. The combination of potassium sulfate aerosol (sp.gr=2.66) and an aluminum foil substrate is believed to be about the worst case from a bounce point of view, that one would encounter in practice, because the aerosol is a hard particle contacting an eleastic metal substrate and because the particle has a relatively high density.

OTHER IMPORTANT DESIGN CONSTRAINTS

A principal teaching of this invention is to limit the value of the bounce parameter so as to eliminate bounce. However, if this were the only constraint, one might have an impactor having turbulent flow around the particles, and/or supersonic flow from the jets would result. Therefore, the design process incorporates two additional limitations. First, the jet stream Reynolds number must be limited to 3200, i.e., to keep gas flow around the particles in the viscous region. This limit on the Reynolds number is a result of the Ranz and wong theory, upon which this work depends, is predicted upon viscous flow around the particles. Cohen and Montan (1967) developed the theory that states that gas flow around the particles will be in the viscous region if the gas flow through the jets has a Reynolds number not greater than 3200. From experience, I consider that it is desirable to have a jet Reynold number no greater than about 1200. Therefore, I have limited the jet Reynolds number to not greater than about 1200.

A second limitation is the Mach number limited to 1.0 A Mach number greater than 1.0 is not possible unless an expanding nozzle is used in the jets. Such a nozzle is impractical to make, and, in addition, there is no available theory with which to calculate the impaction of particles from such a nozzle. In practice, very little is gained by having velocities approaching 1.0. The inventor has found it possible to make a very good design by limiting the Mach number to 0.8.

ELECTROPOLISHING TO ROUND THE UPSTREAM EDGES OF JET HOLES

The entrances to the jet holes 176 may be sharp square edges 177, as shown in FIG. 23, or they may have rounded edges 184 as shown in FIG. 24. As far as is known, all previous impactors have used sharp square edges 177 on jet holes having a diameter smaller than 0.050 inches. If the edges are sharp and square, the abrupt change in velocity of the gas as it enters the jet hole 176 creates some turbulence at the entrance, which in turn cause some of the particulate matter 182 to be prematurely deposited on the upstream face of the jet plate 170. FIG. 22 is a cutaway fragmentary section of the face of a jet plate 170, showing unwanted deposits of particulate matter 182 around the entrances to the holes 176. FIG. 23 is a vertical section across FIG. 22 along line 23—23 and shows the unwanted accumulation of particulate matter 182 and also shows the patterns of tubulent gas flow near the entrance to the hole. By contrast, FIG. 24 shows the smooth air pattern around the entrance to the hole when the entrance is rounded.

For the larger jet hole sizes, countersinking of entrances of jet holes has been described for previous impactors, to avoid this problem of turbulence at the jet hole entrances. However, for hole sizes smaller than about 0.050 inches in diameter, mechanical countersinking is difficult. And, yet the hole sizes on more than half of the jet stages of the present impactor must be smaller than 0.050 inches in diameter in order to make this impactor functional.

Figure 25:
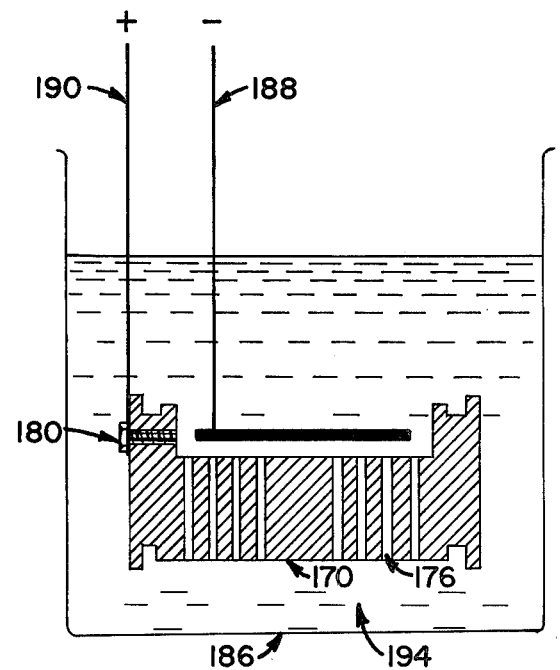
FIG. 25 is a cross-sectional elevational view of a typical jet plate when it is being polished in an electrolyte to round and upstream edges of the jet holes.
Figure 26:
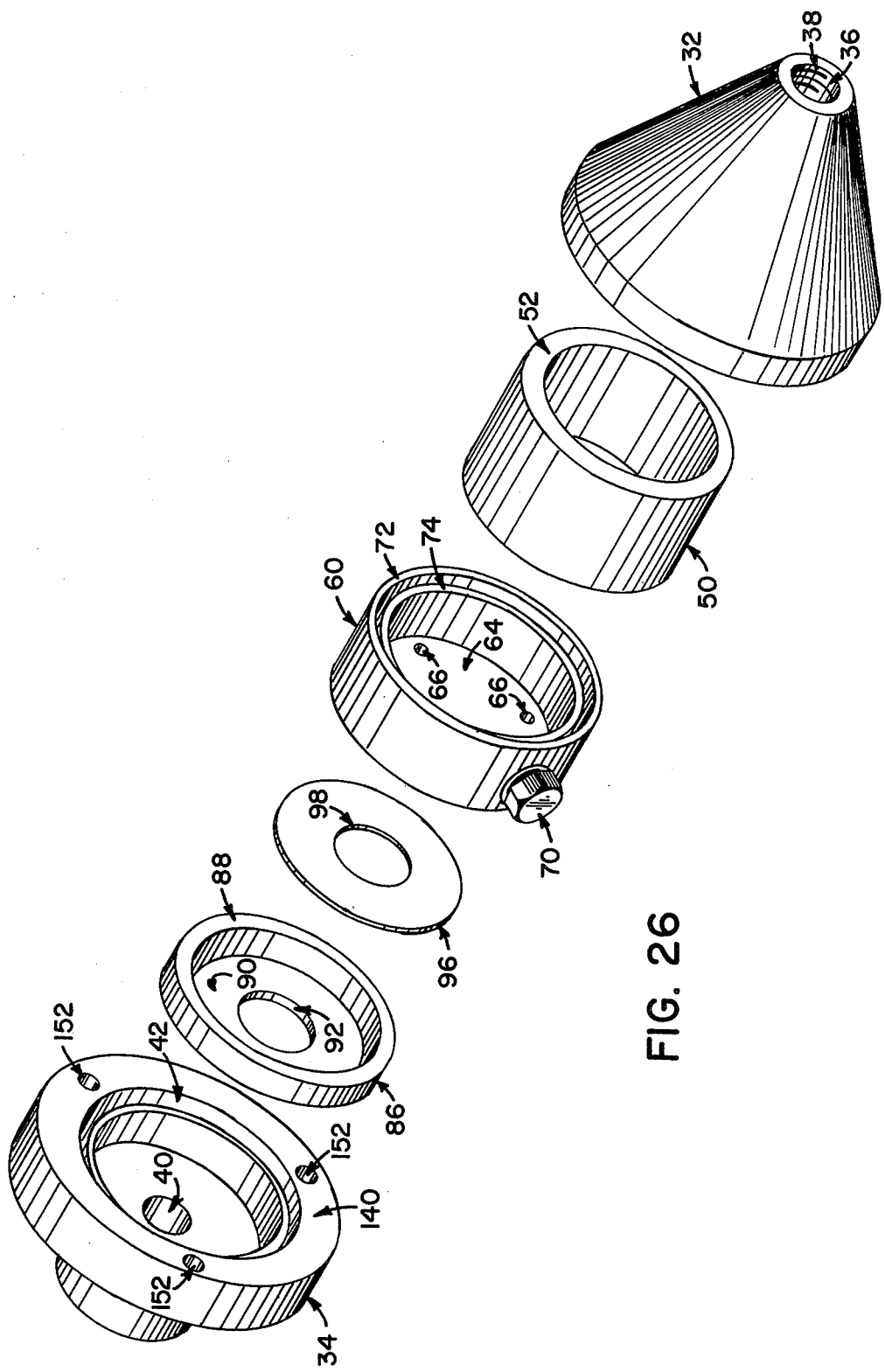
FIG. 26 is an exploded view illustrating the components of the impactor such as the inlet end, the impactor plate, the jet plate, the substrate, the collector plate, and the outlet head.

An innovative feature of this invention is that the upstream edges of jet holes smaller than 0.050 inches diameter are rounded by electropolishing. Electropolishing is a term used by industry to describe the process by which a workpiece is polished by making it the anode in a suitable electrolyte and passing through the part, direct electricla current at a high current density. This process removes metal from the workpiece. The nature of the process is such that edges and protuberances are removed at a faster rate than the metal from the flat part of the workpiece. The relative positions of the workpiece and the other electrical parts during electropolishing, are shown in FIG. 25. The workpiece, a jet stage, is connected to the anode of positive or plus (+) side of the current source. The circuit is completed by placing the cathode very close to but not touching the workpiece and connecting it with the negative or minus (−) side of the current source. The workpiece and the cathode are then immersed in a suitable electrolyte at a suitable temperature.

The choice of electrylyte depends upon the metal that constitutes the workpiece. For aluminum alloys, a solution of 25 grams/liter of fluoboric acid at 86° F. works well. For stainless steel, a solution of sulfuric acid, citric acid and methyl alcohol at 130° F. is very satisfactory. The reference Tegart (1956) states the necessary details concerning electropolishing.

Chemical polishing, that, the polishing by immersion in a chemical solution without the use of an externally applied electromative force or electrical current, is a possible but less satisfactory way to round the entrances to the jet holes. Techniques for chemical polishing are also described by Tegart (1956).

By way of summation, electropolishing or chemical polishing affords a way to round the entrances to even the smallest jet holes and to prevent unwanted deposition of particulate on the upstream faces of the jet plates.

OVERVIEW OF THE DESIGN PROCESS

The teachings of this invention employ several principles which are interdependent. The design process is a systematic and logical organization of these principles and incorporates both experimental and theoretical steps to arrive at a design which will accomplish the objectives of this invention.

The simplest statement of the design process is as follows: The designer chooses the initial design conditions, that is, the number of stages the $d_{50}$ diameter for each stage, initial gas temperature, initial gas pressure, gas flow rate, particle density, maximum jet Reynolds number, and minimum drill size for the jet holes. The design process then selects (1) the number of jet holes in each stage, (2) the diameter of the jet holes in each stage, and (3) the length of the jet holes in each stage, i.e., the thickness of the jet plates and the dimension "t" as illustrated in FIGS. 19 and 21. A detailed description of the design process follows.

THE STEP-BY-STEP DESIGN PROCESS

A step-by-step design process is presented in the following outline.

1. Select the initial design conditions.

a. The designer determines the number of stages and $d_{50}$ value for each stage. A practical general purpose design has a $d_{50}$ diameter of 10,000 nanometers for the first stage. then each succeeding state has a $d_{50}$ diameter one-half the diameter of the preceding stage. This criteria will yield an impactor which will cover the range from 10,000 nanometers to 40 nanometers in nine stages. There is an infinite number of combinations of stages and $d_{50}$ values that may be selected for particular purposes.

b. The designer selects the initial temperature for the inlet. This temperature is usually 70° F., but any reasonable temperature may be used.

c. The designer selects the inlet pressure. A satisfactory inlet pressure value may be less if one were designing the impactor for use at a high altitude.

d. Flow rate of aerosol through the impactor. This quantity is of necessity a comprimise between a high flow rate wanted for securing a representative sample, vacuum pumping system capacity when at very low pressures downstream, the need for low downstream pressure to get impaction of very small particles, and a vacuum pumping system that is portable enough to be carried to a test side. A reasonable comprimise has been a flow rate of 0.35 cfm (measured at inlet conditions) with which can be attained a downstream pressure of 40 Torr, and with which can be impacted a particle of 40 nanometers Stokes diameter.

e. Density of particle to be impacted. Select a value of 2.5 g/cm$^3$ to cover the probable worst case condition, unless the impactor is of a special purpose design for which no particles of greater than 1.0 g/cm$^3$ will be impacted.

f. Maximum jet stream Reynolds number. A value of 1200 recommended.

g. Minimum drill size. A value of 0.−10 inches is recommended. If there will be several stages with very thick jet plates, a larger value of $D_{min}$ may be advisable.

2. Empirically derive the constants required for determination of $C_r$ in the pressure drop equation.

a. Prepare several test jet plate stages. Each stage should have about 70 holes of equal diameter. At least five test stages are required, differing from one another only in the length of the holes (that is, jet plate thickness) and/or in the diameter of the holes. The jet hole diameters should be in the range of 0.010 inch to 0.0135 inch, the plate thicknesses should be in the range of 0.050 inch to 0.50 inch, and the t/D ratio should cover the range between 3 to 35.

b. Electropolish the upstream edges of the test stages if the design will use the electropolished jet holes. In any event, all the test stages should be treated alike, viz., all electropolished or none electropolished.

c. Connect test stages for measurement of pressure drop across the stage as a function of flow rate. Connect equipment with flexible hoses in the following order, from upstream to downstream. (1) dry gas meter, (2) test stage, (3) throttling clamp or valve and (4) vacuum pump. Connect a monometer with one tap between the gas meter and the test stage and the other tap between the test stage and the throttling clamp.

d. Make pressure drop measurements. Turn on vacuum pump and regulate flow with the throttling clamp.

At a number of throttling clamp settings, record the flow rate and the pressure drop across the jet stage. For each test stage, about 20 pairs of observations are suggested, covering Reynolds numbers between 100 and 1500. Repeat steps c. and d. for each of the several test stages.

e. For each observation, calculate Reynolds number:

$$Re_j = \frac{(.5535 \times 10^{-6}) W}{N D T^{.768}}$$

f. For each observation calculate the orifice coefficient:

$$C_v = \sqrt{\frac{1.49 \, W^2 \, T (1 - A_t^2/A_j^2)}{\Delta P \, A_j^2 \, Y^2 \, P_u}}$$

g. Using the data developed in steps a. through f., evaluate the empirical constants $K_1$, $K_2$, $K_3$, $K_4$, and $K_5$, in the equation:

$$C_v = K_1 + K_2 Re_j^2 + K_4(t/D) + K_5(t/D)^2$$

The evaluation may be conveniently done with a stepwise multiple regression computer program, such as the BMDO2R, described by Dixon (1968).

3. For the first stage set $N=1$.
4. Note the value of $d_{50}$ which has been preselected for the first stage. 5. Calculate D for the first stage:

$$D = \sqrt[3]{\frac{.899 \times 10^8 \, C_{50} \rho_p \, d_{50}^2 \, W \, T^{.232}}{\psi_{50} \, P_u}}$$

Readjust D to equal the diameter of the nearest commercially available drill size.

6. Set $t=D$.
7. Calculate $d_{98}$ for the first stage:

$$d_{98} = d_{50} \sqrt{\psi_{98}/\psi_{50}}$$

8. Calculate jet stream Reynolds number:

$$Re_j = \frac{.5535 \times 10^{-6} \, W}{N D T_u^{.768}}$$

9. Calculate orifice coefficient. If D is greater than 0.016 inch, $$C_v = (0.8657 + (0.00002232)(Re_j) - (2.752 \times 10^{-8})(Re_j)^2 + (5.633 \times 10^{-12})(Re_j)^3 - (0.01731)(t/D)^2 + (0.0007474)(t/D)^3 + (0.00007563)(Re_j)(t/D) - (3.005 \times 10^{-6})(Re_j)(t/D)^2 - (1.197 \times 10^{-8})(Re_j)^2(t/D))/(p/D)^{0.1}$$

If D is equal to or less than 0.016 inch, $$C_v = K_1 + K_2(Re_j) + K_3(Re_j)^2 + K_4(t/D) + K_5(t/D)^2$$

10. Calculate the pressure drop across the stage.

$$\Delta P = \frac{(1.49 \, W^2 \, T_u(1 - A_j^2/A_t^2))}{C_v^2 \, A_j^2 \, Y^2 \, P_u}$$

11. Calculate downstream pressure.

$$P_d = P_u - \Delta P$$

12. Calculate downstream temperature. The following calculation assumes the adiabatic expansion of a perfect gas; the calculation was developed from the exposition of Shapiro (1954):

a. Calculate Mach number of gas stream at entrance to jet hole(s):

$$Ma_u = \frac{(.40844) \, W \, T_u^{.5} \, M_w^{.5}}{P_u \, D^2 \, N \, S_r^{.5}}$$

b. Calculate first intermediate variable:

$$A = (S_4 - 1)/2$$

c. Calculate second intermediate variable:

$$B = (P_u Ma_u/P_d)^2(1 + A \, Ma_u^2)$$

d. Calculate the Mach number of gas stream at exit to jet holes(s):

$$Ma_d = ((-1 + (1 + 4A \, B)^{0.5}))/2A)^{0.5}$$

e. Caclulate downstream temperature:

$$T_d = T_u(1 + A \, Ma_u^2)/(1 + A Ma_d^2)$$

13. Note the value of $d_{50}$ that has been preselected for the next stage. Proceed to calculate P, N, and t for the next stage.

14. Calculate D.

$$D = 12.74 d_{50}((C_{50}\rho_p Re_j t \, T_u)/(\psi_{50} P))^{0.5}$$

Readjust D to equal the diameter of the nearest commercially available drill size.

15. Set $t=D$, or $t=0.05$ inch, whichever is the greater.

16. Calculate trial number of holes for the stage in question:

$$N = (0.899 \times 10^8 d_{50}^2 \rho_p W T_u^{0.232})/(D^3 \psi_{50} P_u)$$

Round off N to the nearest integer.

17. Calculate Reynolds number as in step 8.
18. Calculate orifice coefficient, pressure drop, downstream pressure, and downstream temperature as in steps 9, 10, 11, and 12.
19. Recalculate N on the basis of downstream conditions:

$$N = (0.899 \times 10^8 d_{50}^2 \rho_p W T_d^{.232})/(D^3 \psi_{50} P_d)$$

Round off N to the nearest integer.

20. Recalculate $Re_j$ on the basis of downstream conditions:

$$Re_j = (0.5535 \times 10^{-6} W)/(NDT_d^{0.768})$$

21. Repeat steps 18, 19, and 20, until two successive values of N are equal.

22. Calculate the velocity of gas at exit to jet holes:

$$V = (11692 W T_d)/(\pi D^2 P_d N)$$

23. Calculate maximum velocity of gas through jet holes so that particles will not bounce, that is, so that the bounce parameter, $\beta$, will not be exceeded:

$$V_{max} = ((12\beta)/(\rho_p d_{98(j-1)}))^{0.5}$$

24. Calculate $d_{98}$.

$$d_{98} = d_{50}((C_{50}\psi_{98})/(C_{98}\psi_{50}))^{0.5}$$

25. If V is equal to or less than $V_{max}$, go to step 13. If V is greater than $V_{max}$ and D is greater than $D_{min}$, set D equal to the next smaller commercially available drill size and go to step 15. If V is greater than $V_{max}$ and D equals $D_{min}$, go to step 27.

26. Note the preselected value of $d_{50}$ for the next stage. Set t at an initial value of 0.04 inch. Proceed to calculate N and t for the next stage.

27. Add .01 inch to the current value of t.

28. Calculate trial number of holes for the stage in question, as in step 16.

29. Calculate Reynolds number as in step 8.

30. Calculate orifice coefficient, pressure drop, downstream pressure, and downstream temperature as in steps 9, 10, 11, and 12.

31. Recalculate N on the basis of downstream conditions as in step 19.

32. Recalculate Reynolds number on the basis of downstream conditions as in step 20.

33. Repeat steps 30, 31, and 32, until two successive values of N are equal.

34. Calculate velocity of gas at exit to jet holes as in step 22.

35. Calculate maximum velocity of gas from jet holes so as not exceed bounce parameter, as in step 23.

36. Calculate $d_{98}$ as in step 24.

37. If V is greater than $V_{max}$ go to step 27. If V is equal to or less than $V_{max}$ and the stage in question is not the last stage, go to step 26. If V is equal to or less than $V_{max}$ and the stage in question is the last stage, go to step 38.

38. Measure the total pressure drop as a function of flow rate for the vacuum pumping system that will be used with the impactor:

a. Connect equipment for test with flexible hoses in the following order from upstream to downstream. (1) dry gas meter, (2) throttling valve (3) vacuum pumping system. Connect a manometer with one tap between the throttling valve and the vacuum pumping system and the other tap exposed to the ambient air.

b. Close the throttling valve, turn on the vacuum pumping system, and record the pressure drop at zero flow rate. Open throttline valve slightly and record pressure drop and flow rate. Repeat with about a dozen valve settings from maximum pressure drop to about 600 Torr.

c. Using the above data, evaluate the constants $K_6$ and $K_7$ in the equation:

$$\Delta P_{pump} = K_6 + K_7 Q$$

See FIG. 28 for illustration of the curve to be expected.

39. Using the relationship developed in step 38, calculate $\Delta P_{pump}$ for the flow rate that was chosen for the design in question.

40. If the total pressure crop across the impactor, $\Delta P_{tot}$, is greater than $\Delta P_{pump}$, then (1) decrease assumed flow rate through the impactor or (2) increase the $d_{50}$ of the last stage, and go to step 3. If $\Delta P_{tot}$ is less than $\Delta P_{pump}$, then (1) increase assumed flow rate through the impactor or (2) decrease the $d_{50}$ of the last stage and go to step 3.

41. Repeat steps 3 through 40 until $\Delta P_{tot}$ and $\Delta P_{pump}$ agree within $\pm 2$ Torr.

USE OF JET SLITS INSTEAD OF ROUND JET HOLES

Cascade impactors are sometimes made using jet slits instead of round jet holes. FIG. 29 shows a typical jet stage wherein the jet passageways are rectangular slits instead of round holes. FIG. 30 is a cross-sectional view of FIG. 29. Note the jet slit(s) 200. The slits do not need to be rectangular; but may be annular or otherwise curvilinear. The only requirement is that all the slits in a given stage must have the same uniform width.

| NOMENCLATURE | |
|---|---|
| $A_f$ | Total cross sectional area of hole(s) or slit(s) in a given stage (cm$^2$). |
| $A_t$ | Total cross sectional area of the inside of the impactor (cm$^2$). |
| A,B | Intermediate variables in temperature drop calculation; see step 12. |
| C | Cunningham slip correction factor (dimensionless). |
| C = | $1 + \frac{T^{1.268}}{dP}(1.253 \times 10^{-5} + 3.989 \times 10^{-6} \exp(-1.103 \times 10^{-5} \frac{dP}{T^{1.268}}))$ |
| $C_{50}$ | Cunningham factor corresponding to $d_{50}$ |
| $C_{98}$ | Cunningham factor corresponding to $d_{98}$ |
| d | Aerodynamic diameter of particle being impacted (cm, except nanometers when so noted). |
| $d_{50}$ | Particle diameter, 50% of which will be impacted on a given stage. |
| $d_{98}$ | Particle diameter, 98% of which will be impacted on a given stage. |
| D | Diameter of jet hole (cm, except inches where so noted). |
| $D_{min}$ | Minimum diameter of jet hole assumed for a given stage. |
| j | Stage enumerator, that is, j is the stage being considered; j − 1 is the stage immediately upstream from the stage being considered. |
| $K_1, K_2, K_3, K_4, K_5$ | Empirically determined constants in the equation for orifice coefficient for round jet holes. |
| $K_6, K_7$ | Empirically determined constants in the equation for pump performance. |
| $K_8, K_9, K_{10}, K_{11}, K_{12}$ | Empirically determined constants in the equation for orifice coefficient for slit jets. |
| L | Total length of slit(s) in a given stage (cm). |
| $L_1$ | Length of a single slit in a given jet stage. |
| Ma | Mach number, that is, the ratio of the velocity of the gas to the velocity of sound at the same temperature and pressure (dimensionless). |
| $Ma_u$ | Mach number at the entrance to the jet hole(s) or slits of a given stage. |

NOMENCLATURE -continued

| | |
|---|---|
| $Ma_d$ | Mach number at the exit to the jet hole(s) or slits of a given stage. |
| Mw | Molecular weight of the gas (grams per mole). |
| N | Number of round holes in a given jet plate. |
| p | Pitch, that is, center-to-center distance between adjacent holes on a jet plate (cm). |
| P | Absolute static gas pressure (g/cm$^2$, except Torr where so noted). |
| $P_u$ | Pressure upstream from a given stage. |
| $P_d$ | Pressure downstream from a given stage. |
| $\Delta P$ | Pressure drop across a stage. |
| $\Delta P_{tot}$ | Total pressure drop developed across the entire impactor. |
| $\Delta P_{pump}$ | Total pressure drop developed by the vacuum pumping system. |
| Q | Volumetric flow rate through the impactor and/or pump (cm$^3$/sec, expressed at inlet conditions to impactor or outlet conditions to pump). |
| Rej | Reynolds number for the gas stream in a given jet plate with round jet hole(s). See step 8. (dimensionless) |
| Rejt | Target maximum Reynolds number for a given stage. |
| Res | Pseudo-Reynolds number for the gas stream in a given jet stage with slit jets. See substitute step 8 in slit jet design (dimensionless). |
| $S_r$ | Specific heat ratio for the gas (dimensionless). $S_r = 1.403$ for air. |
| t | Length of the jet hole(s) or depth of the jet slit (cm). For jet holes or slits without countersinking or chamfering, t equals the thickness of the jet plate. For jet holes with countersinking, t equals the length of the cylinderical portion of the hole. For jet slits with chamfering, t equals the depth of the section of the slit which has parallel sides. |
| T | Temperature of the gas stream (°K., except °F. where so notes). |
| $T_u$ | Gas temperature upstream from a given stage. |
| $T_d$ | Gas temperature downstream from a given stage. |
| V | Velocity of gas (cm/sec). |
| $V_{max}$ | Maximum velocity of gas so as not to exceed bounce parameter. |
| W | Mass rate of flow of gas (grams/sec). |
| Wi | Width of slit for a given slit jet stage (cm). |
| $Wi_{min}$ | Minimum width of slit assumed for a given design. |
| Y | Gas expansion factor (dimensionless). |
| $Y =$ | $1 - (1 - \dfrac{P_u - \Delta P}{P_u})(.292 + \dfrac{.249 A_j^2}{A_t^2})$ |
| $\beta$ | Nelson bounce parameter (g/sec$^2$). $\beta = \dfrac{\rho_p d_{98(j-1)} V^2}{12}$ |
| $\rho_g$ | Density of gas (g/cm$^3$). |
| $\rho_p$ | Density of particle being impacted (g/cm$^3$). |
| $\mu$ | Viscosity of gas at given temperature (g/sec-cm). |
| $\psi$ | Ranz and Wong impaction parameter of round hole jets. $\psi = \dfrac{C\rho_p d^2 V}{18\mu D}$ |
| $\psi_s$ | Ranz and Wong impaction parameter of slit jets. $\psi_s = \dfrac{C\rho_p d^2 V}{18\mu Wi}$ |
| $\psi_{50}$ | Impaction parameter corresponding to $d_{50}$ for round jets. |
| $\psi_{98}$ | Impaction parameter corresponding to $d_{98}$ for round jets. |
| $\psi_{50s}$ | Impaction parameter corresponding to $d_{50}$ for slit jets. |
| $\psi_{98s}$ | Impaction parameter corresponding to $d_{98}$ for slit jets. |

REFERENCES

J. J. Cohen and D. M. Montan (1967) "Theoretical considerations, design and evaluation of a cascade impactor," Am. Ind. Hyg. Ass. J., 28,95.

W. J. Sixon, (1968)"Biomedical computer programs", University of California Press.

P. A. Nelson, (1973) "A high pressure drop cascade impactor for sizing particles between 0.03 microns and 10 microns in diameter," M.S.E. Thesis, University of Washington, Seattle.

W. J. McG. Tegart (1956) "The Electrolytic and Chemical Polishing of Metals", Pergamon Press, London.

W. J. Ranz and J. B. Wong, (1952) "Impaction of dust and smoke particles on surface and body collectors", Inc. Eng. Chem 44 1371

O. H. Shapiro, (1954) "Dynamics and thermodynamics of compressible fluid flow,"Ronald Press, New York.

| | Date | Patent Number |
|---|---|---|
| Andersen, Ariel A. | Septemper, 1961 | 3,001,914 |
| Lasseur, Claude | September, 1970 | 3,528,279 |
| Pilat, Michael J. | September, 1972 | 3,693,457 |
| Klingler, George A. | November, 1973 | 3,771,291 |
| Andersen, Ariel A. | March, 1974 | 3,795,135 |

W. P. Holland, R. E. Conway; Three Multi-Stage Stack Samplers, Chemical Engineering Progress, Volume 69, No. 6, Pages 93-95

I claim:

1. A cascade impactor for sampling a particle laden gas for particle size distribution, said impactor comprising:

a. a gas inlet and a gas exit;

b. a plurality of stages, each stage comprising a jet plate and a collector plate except that the first jet plate may be a part of or may be replaced by the inlet nozzle;

c. a collector plate downstream from each jet plate, and a jet plate upstream from each collector plate;

d. each jet plate having one or more hole(s) through which the particle laden gas passes wherein said hole(s) are positioned so that the gas from the jet plate is directed to the collector surface on the respective collector plate downstream from said jet plate;

e. a fluid flow path between each collector plate and the jet plate immediately downstream and which path allows relatively unrestrained flow of the particle laden gas from each collector plate to the next succeeding jet plate;

f. appropriate sealing means between a jet plate and a collector plate to cause the gas to flow entirely through the jet plate holes and through the designated passageways between collector plate and succeeding jet plate; and, one or more said jet plates vary in thickness and in which jet plates the jet hole is less than 0.10 inch in diameter and in which the ratio of the length of a jet hole to the diameter of said jet hole to the diameter of said jet hole is greater than 8, and expressed as t/D is greater than 8, and where t is defined as the length of the cylindrical section of the jet hole and for square edged holes, t equals the thickness of the jet plate and with the edges of the jet hole countersunk t is less than the thickness of the jet plate and D is equal to the diameter of the cylindrical section of the jet hole.

2. A cascade impactor according to claim 1 wherein the ratio of the length of any jet hole to the diameter of said jet hole is greater than 10, that is, t/D is greater than 10.

3. A cascade impactor according to claim 1 wherein the ratio of the length of any jet hole to the diameter of said jet hole is greater than 13, that is, t/D is greater than 13.

4. A cascade impactor according to claim 1 wherein the ratio of the length of any jet hole to the diameter of said jet hole is greater than 16, that is, t/D is greater than 16.

5. A cascade impactor according to claim 1 wherein the ratio of the length of any jet hole to the diameter of said jet hole is greater than 20, that is, t/D is greater than 20.

6. A cascade impactor accoring to claim 1 in which the passageway for affording unrestrained flow of gas from a collector plate to the next succeeding jet plate, is a central hole in the collector plate.

7. A cascade impactor according to claim 1 and comprising:

a. each collector surface being covered with a metallic foil; and, b. said foil being held in place within the collector plate by interference fit wherein the outer diameter of the foil is slightly larger than the inner diameter of the collector plate, and the foil is held firmly in place during the sampling period, by having been forced into the collector plate.

8. A cascade impactor according to claim 1 wherein the numbers and sizes of holes in the various jet states are such that with the impactor connected with a predetermined vacuum pumping system and free of a throttling device and appreciable pressure drop between the exit of the impactor and the vacuum pumping system, the impactor will automatically operate at its design flow rate to produce the desired $d_{50}$ separation diameters.

9. A cascade impactor for sampling a particle laden gas for particle size distribution, said impactor comprising:

a. a gas inlet and a gas exit;

b. a plurality of stages, each stage comprising a jet plate and a collector plate except that the first jet plate may be a part or may be replaced by the inlet nozzle;

c. a collector plate downstream from each jet plate, and a jet plate upstream from each collector plate;

d. each jet plate having one or more hole(s) through which the particle laden gas passes wherein said hole(s) are positioned so that the gas from the jet plate is directed to the collector surface on the respective collector plate downstream from said jet plate;

e. a fluid flow path between each collector plate and the jet plate immediately downstream and which path allows relatively unrestrained flow of the particle laden gas from each collector plate to the next succeeding jet plate;

f. appropriate sealing means between a jet plate to cause the gas to flow entirely through the jet plate holes and through the designated succeeding jet plate; and, g. said jet plates vary in thickness and in which jet plates the jet hole is less than 0.050 inch in diameter and the upstream edges of the hole(s) are rounded and flared out to effect a gradual acceleration of the gas into the jet hole, such rounding being accomplished by electropolishing by placing the jet plate in a suitable solution and making the jet plate the anode in a direct current circuit, at a high current density.

10. A cascade impactor according to claim 9 wherein the rounding of the edges of the jet holes is accomplished by placing the jet plate in a suitable chemical solution without the imposition of an electric current.

11. A cascade impactor comprising:

a. a plurality of stages of jet plates and collector plates;

b. said jet plates and said collector plates alternating with each other;

c. a stage comprising a jet plate and a collector plate wherein said jet plate is positioned in front of said collector plate;

d. a jet plate having a first surface and a second surface;

e. said first surface and said second surface being on opposite faces of the jet plate;

f. a peripheral ledge on said first surface;

g. a first groove in said peripheral ledge for receiving a first sealing means;

h. a first sealing means in said first groove;

i. a second groove in said second surface for receiving a second sealing means;

j. a second sealing means in said second groove;

k. said jet plate having a passageway;

l. a collector plate having a central passageway;

m. said collector plate having a first surface for contacting said second sealing means of the immediately preeceding jet plate in said stage and having a second surface for contacting the other first sealing means of the immediately succeeding jet plate in the following stage;

n. said collector plate having a circumscribing shoulder for contacting said second sealing means and a second surface for contacting said first sealing means;

o. said circumscribing shoulder being of a dimension to space the exit surface of said jet plate and the inlet surface of the collector plate a distance at least the diameter of the passageway in the jet plate;

p. said jet plate having a shoulder outside of said ledge and said first groove and said second groove in aligning said jet plate and said collector plate;

q. said circumscribing shoulder being of less diameter than said shoulder of said jet plate thereby making it possible to nest said collector plate with said jet plate for aligning said jet plate and said collector plate; and, r. means to hold said collector plates and said jet plates in an assembled state to form said cascade impactor.

12. A cascade impactor for sampling a particle laden gas for particle size distribution, said impactor comprising:

a. a gas inlet and a gas outlet;

b. a plurality of stages, each stage comprising a jet plate and a collector plate except that the first jet plate may be a part of or may be replaced by the inlet nozzle and the jet plates in those stages past the first stage vary in thickness with respect to each other;

c. a collector plate downstream from each jet plate, and a jet plate upstream from each collector plate;

d. each jet plate having one or more hole(s) through which the particle laden gas passes wherein said hole(s) are positioned so that the gas from the jet plate is directed to the collector surface on the respective collector plate downstream from said jet plate;

e. a fluid flow path between each collector plate and the jet plate immediately downstream and which path allows relatively unrestrained flow of the particle laden gas from each collector plate to the next succeeding jet plate;

f. appropriate sealing means between a jet plate and a collector plate to cause the gas to flow entirely through the jet plate holes and through the designated passageways between collector plate and succeeding jet plage; and, g. said cascade impactor having the characteristics that the value of the bounce parameter, $\beta$, never exceeds 300 g/sec$^2$, where:

$$\beta = \frac{\rho_p d_{m(j-1)} V^2}{12} = \text{Nelson bounce parameter}$$

$\rho_p$ = specific gravity of particles being impacted, g/cm$^3$ $d_{m(j-1)}$ = diameter of particle which has an m percent probability of being captured on the stage immediately upstream from the stage being considered, cm V = average velocity of the jet stream at the point of exit of the stream from the jet plate of the stage being considered, cm/sec.

13. A cascade impactor according to claim 12 wherein m is equal to 98% probability of being captured.

14. A cascade impactor according to claim 13 wherein $\beta$ never exceeds 400 g/sec$^2$.

15. A cascade impactor according to claim 13 wherein $\beta$ never exceeds 500 g/sec$^2$.

16. A cascade impactor according to claim 13 wherein $\beta$ never exceeds 600 g/sec$^2$.

17. A cascade impactor according to claim 13 wherein $\beta$ never exceeds 800 g/sec$^2$.

18. A cascade impactor according to claim 13 wherein $\beta$ never exceeds 1000 g/sec$^2$.

19. A cascade impactor for sampling a particle laden gas for particle size distribution, said impactor comprising:

a. a gas inlet and a gas exit;

b. a plurality of stages, each stage comprising a jet plate and a collector plate except that the first jet plate may be a part of or may be replaced by the inlet nozzle;

c. a collector plate downstream from each jet plate, and a jet plate upstream from each collector plate;

d. one or more of said jet plates having one or more square or rectangular slits through which the particle laden gas passes, such slit being positioned so that the gas from the jet plate is directed to the collector surface on the respective collector plate downstream from said jet plate;

e. a fluid flow path between each collector plate and the jet plate immediately downstream and which path allows relatively unrestrained flow of the particle laden gas from each collector plate to the next succeeding jet plate;

f. appropriate sealing means between a jet plate and a collector plate to cause the gas to flow entirely through the jet plate holes and through the designated passageways between collector plate and succeeding jet plate; and, g. one or more said jet plates vary in thickness in which jet plates the jet slit is less than 0.10 inch in width and in which the ratio of the depth of a jet slit to the width of said jet slit is greater than 8, and expressed at t/Wi is greater than 8 and where t is defined as the depth of the section of the jet slit that has parallel sides and for square edged slits, t equals the thickness of the jet plate and with the edges of the slits chamfered, t is then the thickness of the jet plate and Wi is equal to the width of the section of the jet slit that has parallel sides.

20. A cascade impactor according to claim 19 wherein the ratio of t/Wi is greater than 10.

21. A cascade impactor according to claim 19 wherein the ratio t/Wi is greater than 13.

22. A cascade impactor according to claim 19 wherein the slits have a constant width, Wi, and have a curvilinear configuration.

23. A method for determining particle sizes of particular matter in gas in the atmosphere, said method comprising:

a. varying the direction of the velocity of the gas and the particulate matter in the jet stream to separate the particulate matter from gas to form separated particulate matter;

b. collecting the separated particulate matter and weighing the separated particulate matter;

c. repeating the varying of the direction and the velocity of the gas and the particulate matter to separate different sizes of particulate matter;

d. controlling the velocity of the gas and the particulate matter to have a value for the bounce parameter, $\beta$, less than 300 g/sec$^2$, wherein:

$$\beta = \frac{\rho_p \, d_{m(j-1)} \, V^2}{12} = \text{Nelson bounce parameter}$$

$\rho p$ = specific gravity of particles being impacted, g/cm$^3$ $d_{m(j-1)}$ = diameter of a particle which has an m percent probability of being captured on the stage immediately upstream from the being considered, cm V = average initial velocity of the jet stream at the stage being considered, cm/sec; and, e. causing the gas to flow in jet passageways with the length to diameter ratios greater than eight, thereby causing the static pressure of the gas downstream from the passageways to be reduced thereby causing the cunningham slip correction factor to be increased, thereby causing the velocity required for impaction of a given diameter particle to be reduced, thereby causing the 62 (beta) bounce parameter to be reduced to a level such that bounce of the particles will not occur.

* * * * *